US008012486B2

(12) United States Patent
Lee et al.

(10) Patent No.: US 8,012,486 B2
(45) Date of Patent: Sep. 6, 2011

(54) COMPOSITION FOR TREATING ATOPIC DERMATITIS COMPRISING HIRSUTENONE AS AN ACTIVE INGREDIENT

(75) Inventors: Min Won Lee, Seoul (KR); Young Wook Choi, Seoul (KR); Seong Jun Seo, Anyang-si (KR); Do Ik Lee, Seoul (KR); Hyoweon Bang, Seoul (KR); Chung Soo Lee, Seoul (KR); Jong Chan Lee, Seoul (KR); Soon-Chul Myung, Sungnam-si (KR); Mi-Kyung Lee, Seoul (KR); Seong Soo Joo, Suwon-si (KR); Sun Eun Choi, Seoul (KR)

(73) Assignee: Chung-Ang University Industry Academic Cooperation Foundation, Seoul (KR)

( * ) Notice: Subject to any disclaimer, the term of this patent is extended or adjusted under 35 U.S.C. 154(b) by 0 days.

(21) Appl. No.: 12/454,520

(22) Filed: May 19, 2009

(65) Prior Publication Data
US 2010/0190862 A1    Jul. 29, 2010

(30) Foreign Application Priority Data
Jan. 28, 2009    (KR) .................. 10-2009-0006646

(51) Int. Cl.
A61K 39/00    (2006.01)
A61K 8/02    (2006.01)
A61K 47/00    (2006.01)
A61K 31/12    (2006.01)
(52) U.S. Cl. .................. 424/184.1; 424/401; 424/439; 514/679

(58) Field of Classification Search .................. None
See application file for complete search history.

(56) References Cited

U.S. PATENT DOCUMENTS
2005/0215635 A1* 9/2005 Rafi et al. .................. 514/546

OTHER PUBLICATIONS

"Inhibition of activated responses in dendritic cells exposed to lipopolysaccharide and lipoteichoic acid by diarylheptanoid oregonin", J. Int. Immunopharmacology (2008) 8, 748-755 to Choi et al.*
"In vivo expression of IL-12 and IL-13 in atopic dermatitis", J. Allergy Clin. Immunol., 7 (1996) 225-231 to Hamid et al.*
"Preparation and anti-inflammatory activities of diarylheptanoid and diarylheptylamine analogs", Bioorganic and Medicinal Chemistry, 13 (2005), 6175-6181 to Lee et al.*
Choi et al., "Cytotoxic Activities of Diarylheptanoids from *Alnus japonica*," Arch. Pharm. Res. 31:1287-1289, 2008.

(Continued)

*Primary Examiner* — Shengjun Wang
*Assistant Examiner* — Svetlana M Ivanova
(74) *Attorney, Agent, or Firm* — Clark & Elbing LLP

(57) ABSTRACT

The present invention relates to a composition for treating atopic dermatitis comprising hirsutenone as an active ingredient. Hirsutenone as the active ingredient of the present composition decreases the number of eosinophil and the level of IgE increased in atopic dermatitis and remarkably reduces expression amounts of immune regulatory cytokine (e.g., IL-4, IL-5 and IL-13) associated with atopic dermatitis. In addition, hirsutenone decreases COX-2 and iNOS expression. Hirsutenone as the active ingredient of the present composition could be effectively used in drugs, cosmetics and foods for treating atopic dermatitis or relieving a symptom of atopic dermatitis.

4 Claims, 42 Drawing Sheets
(20 of 42 Drawing Sheet(s) Filed in Color)

OTHER PUBLICATIONS

Kim et al., "Hirsutenone Inhibits Phorbol Ester-Induced Upregulation of COX-2 and MMP-9 in Cultured Human Mammary Epithelial Cells: NF-κB as a Potential Molecular Target," FEBS Lett. 580:385-392, 2006.

Kim et al., "Nitric Oxide and Prostaglandin $E_2$ Synthesis Inhibitory Activities of Diarylheptanoids from the Barks of *Alnus japonica* Steudel," Arch. Pharm. Res. 28:177-179, 2005.

* cited by examiner

Brown amorphous powder, $[\alpha]^{20}_D$ : 12.8° (C=1.0, Me$_2$CO)
IR$^{KBr}_{max}$ cm-1 : 3367(OH), 1701(C=O) 1605, 1522(Aromatic C=C)

Brown amorphous powder, $[\alpha]^{20}_D$: -14.9° (C=1.0, Me$_2$CO)
IR$^{KBy}_{max}$ cm-1 : 3367(OH), 1701(C=O), 1605, 1522(Aromatic C=C)

$^1$H-NMR spectrum (Me$_2$CO-d$_6$ + D$_2$O, 300 MHz)

$^{13}$C-NMR spectrum (Me$_2$CO-d$_6$ + D$_2$O, 75 MHz)

Fig. 3a

Prepare extract from bark or leaves of *Alnus japonica*

Dilute enzyme stock solution (10ml) with Distilled Water (1L)

Mix the extract from *Alnus japonica* with diluted enzyme solution and react it at room temperature overnight (24 hrs)

Recover supernatant by centrifuging the enzyme reaction solution

Extract the supernatant solution with ethyl acetate

Concentrate the extract solution

Fig. 3c mixed products (nonol+none) 1g
|
S-1

Fr.1 — Hirsutanonol (1) — 620mg — yeild (62%)

Fr.2 — Hirsutenone (2) — 380mg — yeild (38%)

| Chromato. Gel | Solvent system |
|---|---|
| S : Sephadex LH-20 | 1 : 60% MeOH |

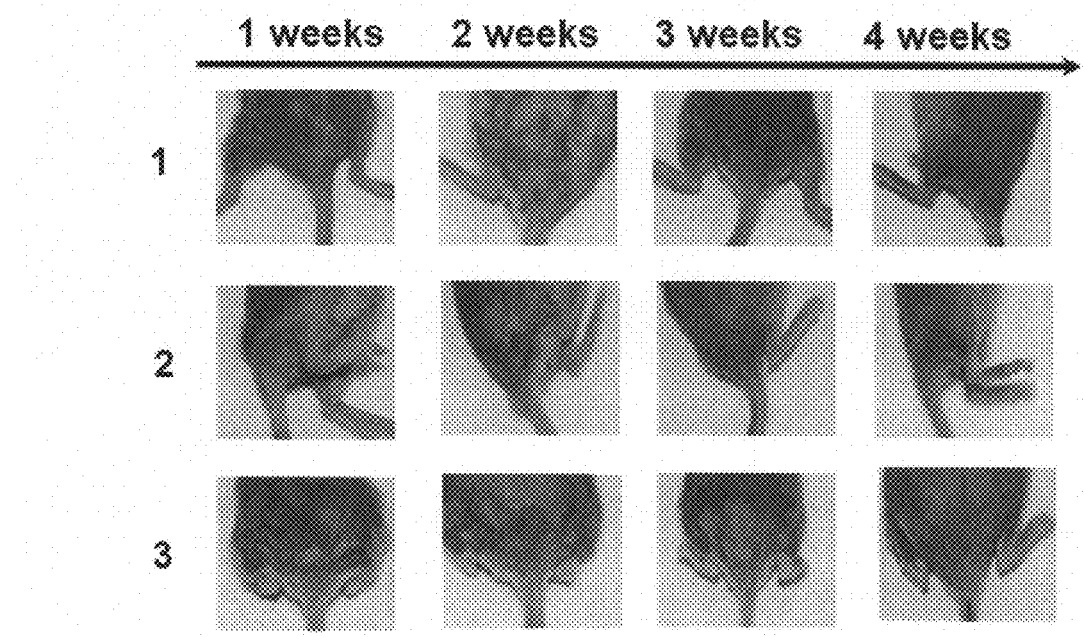

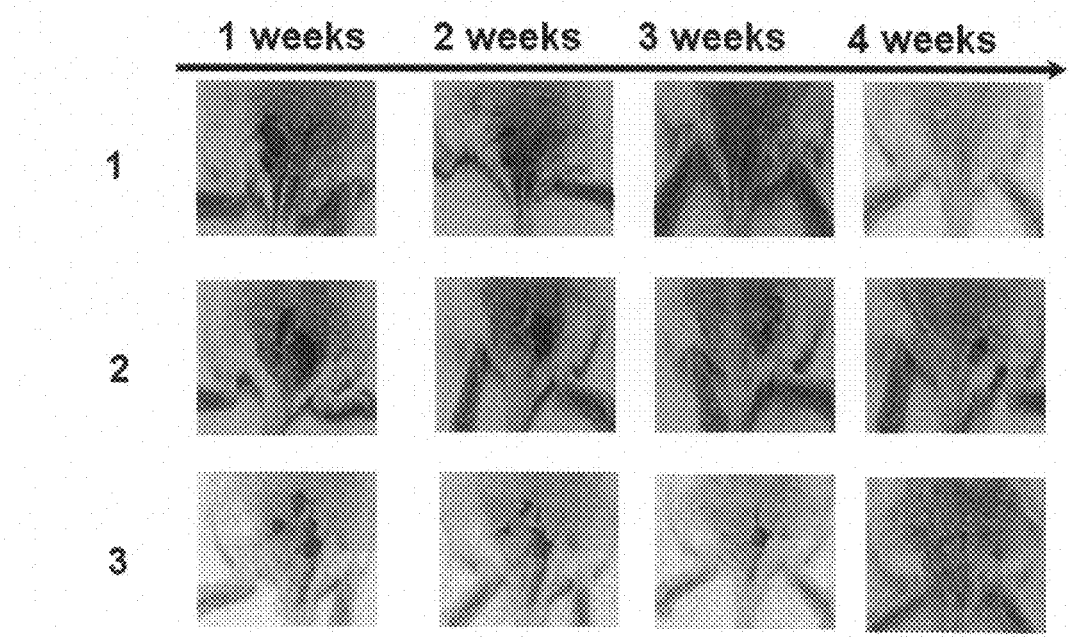

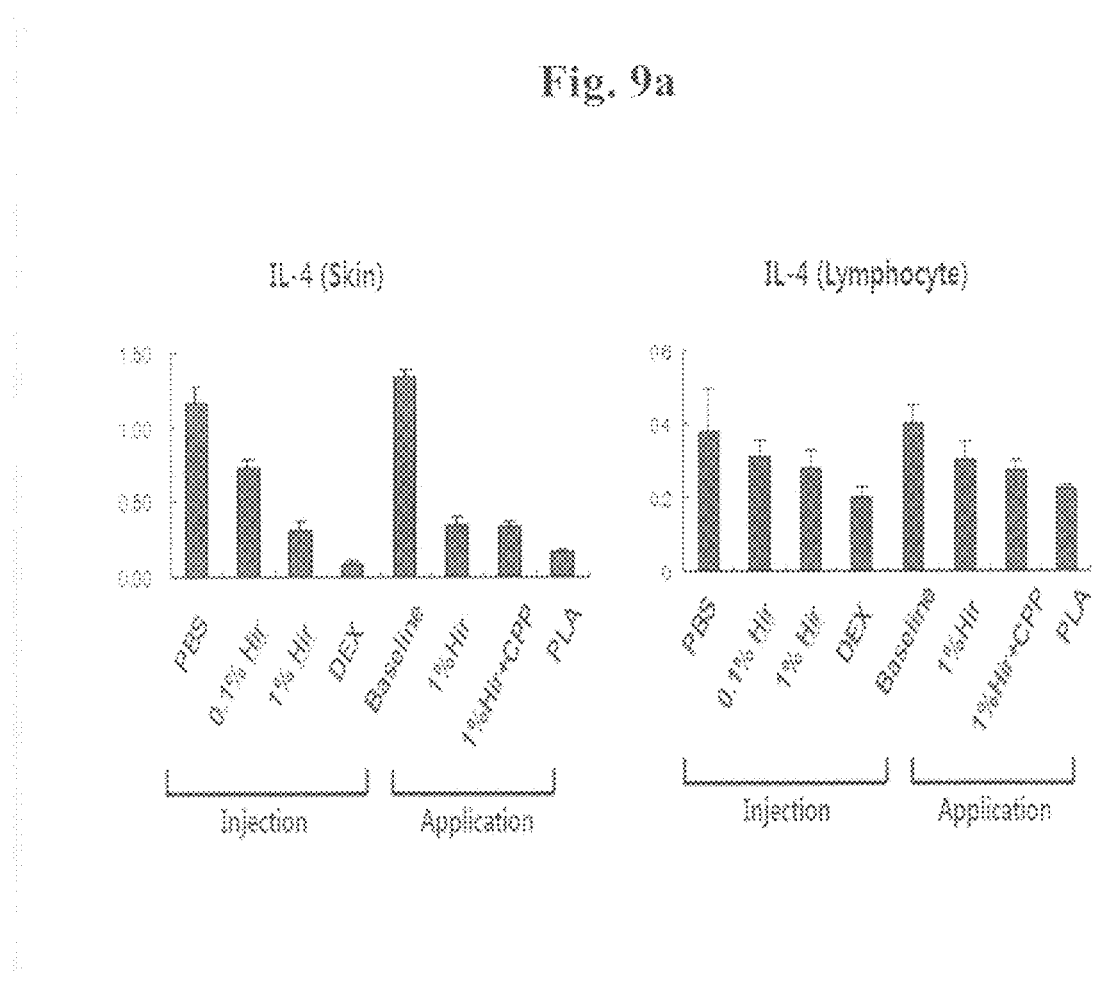

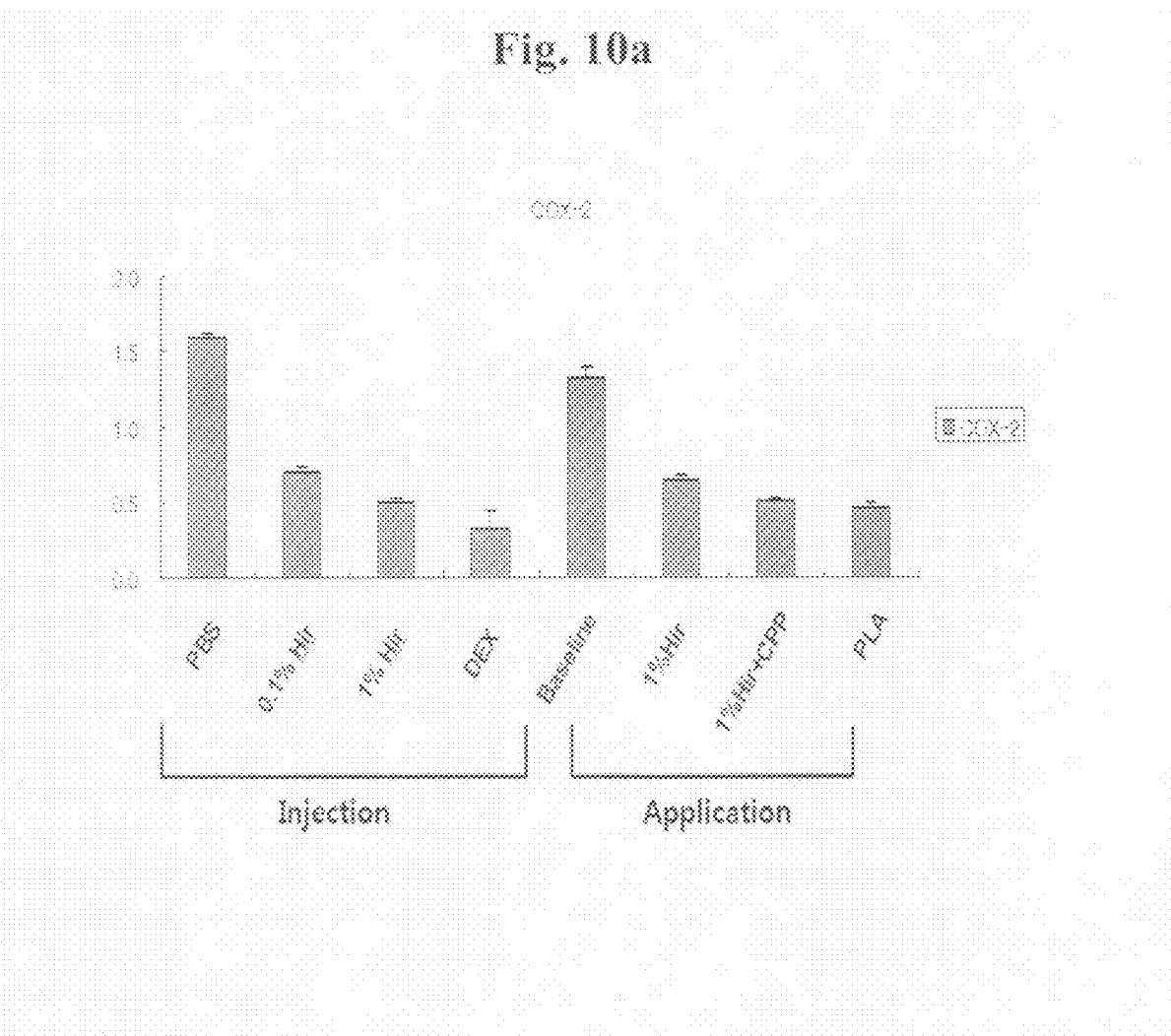

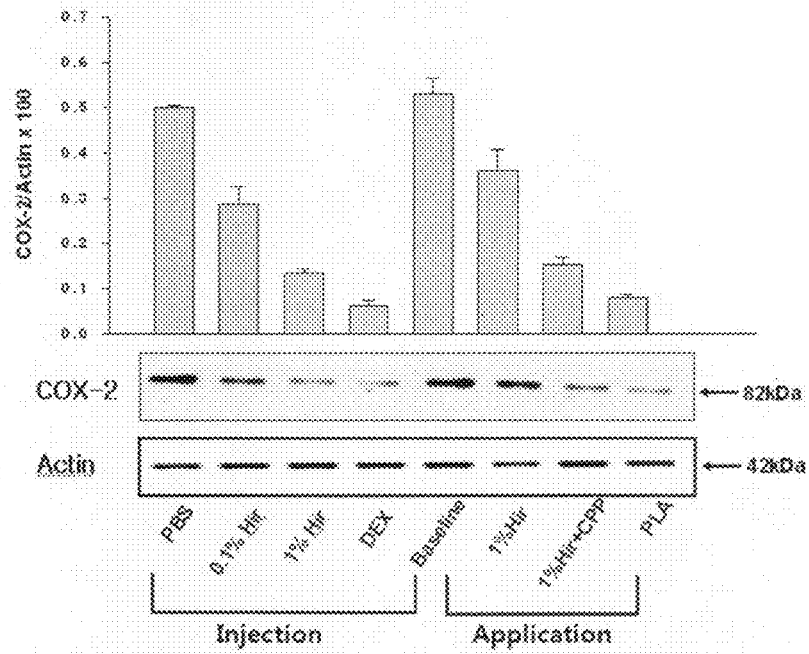

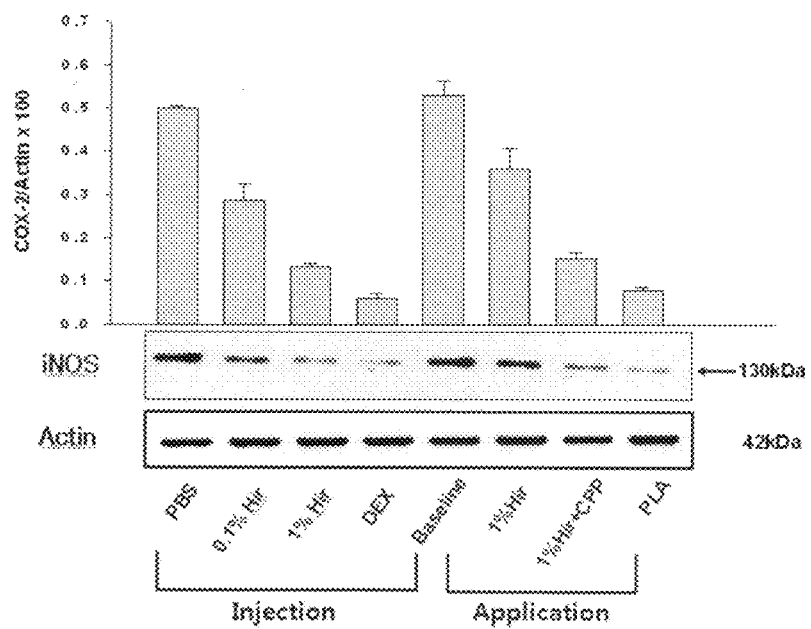

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
acataaagga cgagcgatgg                                                   20

```
<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
tgcagatggg gtgtcataga                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gccatgagga ctctctgctc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
aggggttctt ctctgggaaa                                              20

<210> SEQ ID NO 5
<211> LENGTH: 20
<212> TYPE: DNA
<213> ORGANISM: Artificial Sequence
<220> FEATURE:
<223> OTHER INFORMATION: Standard Construct

<400> SEQUENCE: 5
tcagattggc agttgtggag                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
gctagggagc acttgtttgc                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
ctgatgcctc ttccaggtgt                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 8
gagggagccc tttctgaatc                                              20

<210> SEQ ID NO 9
<211> LENGTH: 24
<212> TYPE: DNA
<213> ORGANISM: Artificial Sequence
<220> FEATURE:
<223> OTHER INFORMATION: Synthetic Construct

<400> SEQUENCE: 9
ccacccatgg caaattccat ggca                                         24

<210> SEQ ID NO 10
<211> LENGTH: 32
<212> TYPE: DNA
<213> ORGANISM: Artificial Sequence
<220> FEATURE:
<223> OTHER INFORMATION: Synthetic Construct

<400> SEQUENCE: 10
ggtgctgctt gttaggaggt caagtaaagg gc                                32

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11
ccacccatgg caaattccat ggca                                         24

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ccctgttgct gtagccgtat                                              20
```

COMPOSITION FOR TREATING ATOPIC DERMATITIS COMPRISING HIRSUTENONE AS AN ACTIVE INGREDIENT

BACKGROUND OF THE INVENTION

1. Field of the Invention

The present invention relates to a composition for treating atopic dermatitis comprising hirsutenone as an active ingredient.

2. Background of the Invention

Hirsutenone belongs to compounds having a structure of diarylheptanoid extracted from stem bark of the genus *Alnus*. Asakawa et al. islolated four kinds of compounds (e.g., alnustone) involving a new structure of diarylheptanoid extracted from flower of *A. pendula* in 1972 and Miyake et al. in 1973 reported that hirsutenone and hirsutenone were isolated from green stem bark of *A. hirsute* (Suga, T., Iwata, N. and Asakaw, Y.: Chemical constituents of male flower of *Alnus pendula*. *Bull. Chem. Soc. Jap.*, 45, 2058-2060, 1972).

Doug et al. discovered that diarylheptanoid plays a critical role in strong prevention of platelet coagulation in 1998 (Doug, H., Chen, S. X., Xu, H. X., Kadota, S. and Namba, T.: A new antilplatelet diarylheptanoid from *Alpinia blepharocalyx*. *J. Nat. Prod.*, 61, 142-144, 1998).

In addition, Lee et al. reported diarylheptanoid as a new PKC alpha inhibitor in 1998 (Lee, K. K., Bahler, B. D., Hofmann, G. A., Mattern, M. R., Johnson, R. K. and Kingston, D. G. I.: Isolation and structure elucidation of new PKCα inhibitor from *Pinus flexilis*. *J. Nat. Prod.*, 61, 1407-1409, 1998).

Surh et al. in 1999 and Ishida et al. in 2000 also found that diarylheptanoids have an antitumor-promoting potential (Chun, K.-S., Sohn, Y.-S., Kim, H.-S., Kim, O.-H., Park, K.-K., Lee, J.-M., Lee, J., Lee, J.-Y., Moon, A., Lee, S.-S, and Surh, Y.-J.: Antitumor promoting potential of naturally occurring diarylheptanoids structurally related to curcumin, *Mutation Research*, 428, 49-57, 1999; Ishida, J. Kozuka, M., Wang, H.-K., Konoshima, T., Tokuda, H., Okuda, M., Mou, X. Y., Nishino, H., Sakurai, N., Lee, K.-S, and Nagai, M.: Antitumor-promoting effects of cyclic diarylheptanoids on Epstein-Barr virus activation and two-stage mouse skin carcinogenesis, *Cancer Letters*, 159, 135-140, 2000).

The term "atopy" refers to a meaning to be "extraordinary" or "inappropriate" on etymology. Atopic dermatitis is a chronic inflammatory disease which repeats improvement and aggravation after its attack in babyhood or infancy, and is diagnosed according to three features of individual or familial atopy, severe itching and eczema. In addition, atopic dermatitis could be worsen by infection, mental stress, changes of season and weather, stimulation and allergy.

The etiology of atopic dermatitis remains to be clearly elucidated, but according to recent researches, the reasons of attack to induce atopic dermatitis are as follows: (a) hypersensitive response caused from increase of IgE antibody, (b) functional defect by irregular differentiation of T lymphocyte which is caused from reduction of cell-mediated immune response, and (c) blocking of adrenal receptor present in the skin. Therefore, atopic dermatitis has been thought to be a hereditary disorder generated by immunological abnormality.

In general, humectant to preserve the moisture on the skin and steroid hormone (e.g., local antenatal corticosteroid) to alleviate inflammation response are simultaneously treated in most dermatologic clinic for treatment and management of atopic dermatitis. Using a local antenatal corticosteroid for a long period, it is a serious problem to produce various side effects on skin such as dermal atrophy, vasodilatation, depigmentation and striae distensae. Therefore, it has been endeavored to develop a raw material or a drug with anti-inflammatory efficacy for treating atopy without these side effects.

It has been disclosed that hirsutenone compounds have anti-cancer function and anti-oxidative activity, but their physiological effects on atopic dermatitis have not been reported yet.

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to develop a compound for treating atopic dermatitis from natural extracts. As results, we have discovered that hirsutenone, a diarylheptanoid compound among compounds contained in the extract from stem barks or leaves of *Alnus japonica*, regulates an expression level of immune cytokines associated with atopic dermatitis and treats atopic dermatitis or alleviates a symptom of atopic dermatitis through its regulatory activities.

Accordingly, it is an object of this invention to provide a composition for treating atopic dermatitis, comprising hirsutenone as an active ingredient.

Other objects and advantages of the present invention will become apparent from the following detailed description together with the appended claims and drawings.

In one aspect of this invention, there is provided a pharmaceutical composition for treating or preventing atopic dermatitis comprising: (a) a therapeutically effective amount of an isolated hirsutenone; and (b) a pharmaceutically acceptable carrier.

In another aspect of this invention, there is provided a cosmetic composition for relieving atopic dermatitis comprising: (a) a cosmetically effective amount of an isolated hirsutenone; and (b) a cosmetically acceptable carrier.

In still another aspect of this invention, there is provided a functional food composition for relieving atopic dermatitis, comprising an isolated hirsutenone as an active ingredient.

In still another aspect of this invention, there is provided a method for treating atopic dermatitis in a subject suffering from atopic dermatitis, which comprises contacting said subject with a composition comprising a therapeutically effective amount of an isolated hirsutenone or administering said composition to said subject.

In still another aspect of this invention, there is provided a method for relieving a symptom of atopic dermatitis in a subject suffering from atopic dermatitis, which comprises contacting said subject with a composition comprising an isolated hirsutenone or administering said composition to said subject.

The present inventors have made intensive studies to develop a compound for treating atopic dermatitis from natural extracts. As results, we have discovered that an isolated hirsutenone, a diarylheptanoid compound among compounds contained in the extract from stem barks or leaves of *Alnus japonica*, regulates expression levels of immune cytokines associated with atopic dermatitis and also treats atopic dermatitis or alleviates a symptom of atopic dermatitis through its regulatory activity.

Hirsutenone used as the active ingredient of the present composition is an isolated compound represented by the following formula 1.

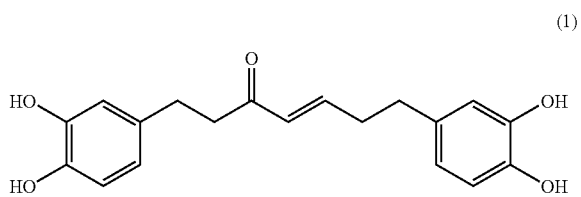

(1)

Hirsutenone as the active ingredient of the present composition could be obtained from natural products, for example extracts of stem barks or leaves of *Alnus japonica*. It is well known to those skilled in the art that chemically synthesized hirsutenone could also have the same effect as much as one obtained from extracts have.

The extract from stem bark of *Alnus japonica* in this invention may be prepared according to a conventional method known in the art, for example utilization of solvent under conditions of typical temperature and pressure. In general, the conventional solvent involved in extraction process is used as the extraction solvent for isolating stem bark extracts of *Alnus japonica*, and preferably is selected from the groups consisting of water, anhydrous or hydrated lower alcohol containing 1 to 4 carbon atoms, acetone, ethylacetate, butylacetate and 1,3-butylene glycol.

In addition, hirsutenone as an active ingredient of the present composition may be obtained from enzymatic reaction in which xylose is removed from oregonin compounds represented by the following formula 2.

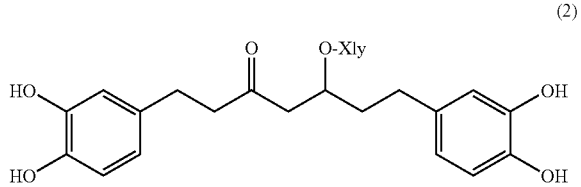

(2)

Hirsutenone as an active ingredient of the present composition decreases the number of eosinophil and the expression level of IgE increased in atopic dermatitis and remarkably reduces the level of immune regulatory cytokines, IL-4, IL-5 and IL-13 associated with atopic dermatitis. In addition, hirsutenone reduces the expression levels of COX-2 and iNOS.

The composition of this invention may be provided as a pharmaceutical composition. The term "pharmaceutically effective amount" refers to an amount enough to show and accomplish efficacies and activities of the compound of this invention for treating or preventing atopic dermatitis. The pharmaceutical composition of this invention includes a pharmaceutically acceptable carrier besides the active ingredient compound.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.001-200 mg/kg (body weight).

The pharmaceutical composition according to the present invention may be administered orally or parenterally, and preferably, administered parenterally, e.g., by intravenous, intraperitoneal, intramuscular, intra-abdominal or transdermal.

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

According to a preferable embodiment, the pharmaceutical composition of the present invention is formulated for a skin application. The skin application is not particularly limited and preferably includes a powder, a gel, an ointment, a cream, a fluid or an aerosol.

The composition of this invention may be provided as a cosmetic composition. The term used herein "cosmetically effective amount" refers to an amount enough to accomplish efficacies on improvements in atopic dermatitis described hereinabove.

The pharmaceutical composition of this invention includes a cosmetically acceptable carrier besides the active ingredient compound.

The cosmetic compositions of this invention may be formulated in a wide variety of forms, for example, including a solution, a suspension, an emulsion, a paste, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softner, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as compounds as active ingredients and carriers. The non-limiting examples of auxiliaries include antioxidants, stabilizers, solubilizers, vitamins, colorants, odor improvers or mixtures of these substances.

The composition of the present invention may be provided as a food composition, particularly a functional food composition. The functional food composition of the present invention may be formulated in a wide variety of forms, for example, including proteins, carbohydrates, fatty acids, nutrients and seasoning agents. In the formulation of drinking agent, it may further include a flavoring agent or natural carbohydrates. For instance, natural carbohydrate may include monosaccharides (e.g., glucose, fructose, etc.); disaccharides (e.g., maltose, sucrose, etc.); oligosaccharides; polysaccharides (e.g., dextrin, cyclodextrin, etc.); and sugar alcohols (e.g., xylitol, sorbitol, erythritol, etc.). The formulation of flavoring agent may use natural flavoring agents (e.g., thaumatin, stevia extract, etc.) and synthetic flavoring agents (e.g., saccharine, aspartame, etc.). The food composition of the present invention may be much effectively utilized to improve or alleviate atopic dermatitis.

The features and advantages of the present invention will be summarized as follows:

(i) The composition of this invention provides a new use of hirsutenone for treating atopic dermatitis or relieving a symptom of atopic dermatitis.

(ii) Hirsutenone as an active ingredient of the present composition decrease the number of eosinophil and the expression level of IgE increased in atopic dermatitis and remarkably reduces expression of immune regulatory cytokines, IL-4, IL-5 and IL-13 associated with lesion of atopic dermatitis.

(iii) Hirsutenone as an active ingredient of the present composition also decreases COX-2 and iNOS expression in mouse model of atopic dermatitis.

(iv) Hirsutenone as an active ingredient of the present composition could be effectively used in drugs, cosmetics and foods for treating or alleviating a symptom of atopic dermatitis.

The present invention relates to a composition comprising hirsutenone as an active ingredient for treating atopic dermatitis or relieving a symptom of atopic dermatitis. Hirsutenone as an active ingredient of the present composition decreases the number of eosinophil and the expression level of IgE increased in atopic dermatitis and remarkably reduces expression level of immune regulatory cytokines, IL-4, IL-5 and IL-13 associated with atopic dermatitis. In addition, hirsutenone decreases COX-2 and iNOS expression. Hirsutenone as an active ingredient of the present composition could be effectively used in drugs, cosmetics and foods for treating or alleviating atopic dermatitis.

BRIEF DESCRIPTION OF THE DRAWINGS

The file of this patent or application publication contains at least one drawing executed in color. Copies of this patent or application publication with color drawing(s) will be provided by the Office upon request and payment of the necessary fee.

FIGS. 3a and 3b represent a flow chart to obtain hirsutenone and hirsutanonol through enzymatic hydrolysis of oregonin.

FIG. 3c schematically represents a process to extract hirsutenone and hirsutanonol from an enzymatic lysate of oregonin.

FIG. 5f is photographs showing treatment effect on atopic dermatitis after 1% hirsutenone was applied to the skin of NC/Nga mouse in which the atopic dermatitis had been induced.

FIG. 6d is photographs showing treatment effect on atopic dermatitis after dexamethasone was injected into BALB/c mouse in which the atopic dermatitis had been induced as a positive control.

FIG. 9a is a graph showing IL-4 level measured by ELISA in the skin and lymph node obtained from each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.

FIG. 10a is a graph showing a COX-2 mRNA level detected by real-time PCR in each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.

FIG. 11a is a graph showing a COX-2 protein level measured by ELISA in each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.

FIG. 11d is a graph showing iNOS protein level measured by ELISA in each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.

Figure 1A:
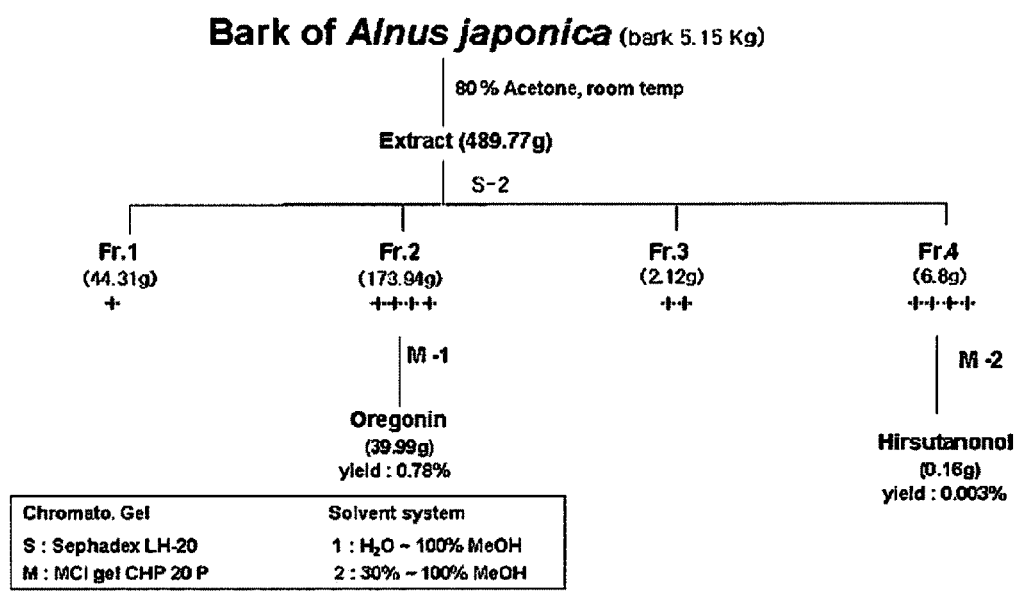
FIG. 1a schematically represents a process to extract and purify oregonin from the stem bark of *Alnus japonica*.
Figure 1B:
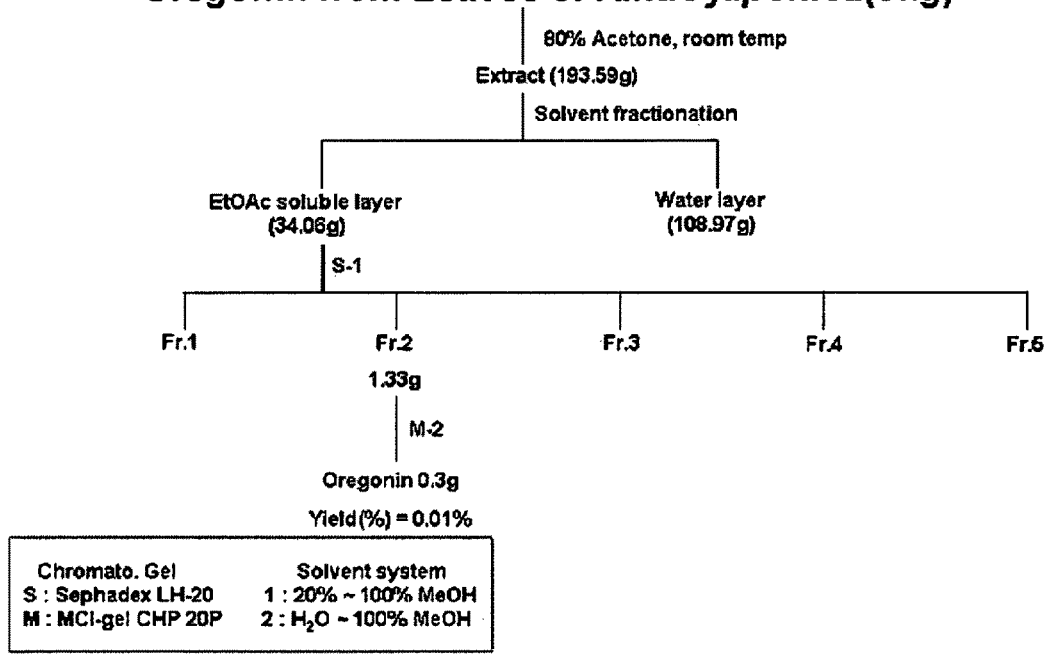
FIG. 1b schematically represents a process to extract and purify oregonin from leaves of *Alnus japonica*.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Methods

1. Experimental Materials

The stem bark of *Alnus japonica* used for the extraction of an active ingredient of hirsutenone was collected in Sudal mountain, dongjak-gu, Seoul on June, 2008 and confirmed by plant judgement.

2. Instruments and Reagents

The instruments and reagents used in the examples were as follows:

TABLE 1

Instruments and reagents used in this invention

| | |
|---|---|
| Balance | Sartorius AC211S (Germany) |
| Centrifuge | Eppendorff 5415D (Germany) |
| Liquid chromatography mass spectrometer | API 3000 triple quadrupole liquid chromatography mass spectrometry (Canada) |
| $^1$H-NMR spectrometer | Varian Gemini 2000, 300 MHz (USA) Bruker AMX-500, 500 MHz (Germany) Solvent: DMSO-$d_6$, $D_2O$, Acetone-$d_6$ Internal standard: TMS |
| $^{13}$C-NMR spectrometer | Varian Gemini 2000, 75 MHz (USA) Bruker AMX-500, 125 MHz (Germany) Solvent: DMSO-$d_6$, $D_2O$, Acetone-$d_6$ Internal standard: TMS |
| TLC Adsorbent | Kieselgel 60 $F_{254}$ (Merck, Germany) |
| TLC Solvent(v/v) | $CHCl_3$:MeOH:$H_2O$ = 70:30:4 $CHCl_3$:MeOH:$H_2O$ = 6:4:1 Benzene:Ethylformate:Formic acid = 1:7:1 |
| TLC Detection | Ethanolic-$FeCl_3$ solution 10%-$H_2SO_4$ in ethanol (heating) UV-lamp (254 nm) |
| Gels | Sephadex LH-20 (25-100 μm, Pharmacia, Sweden) MCI gel CHP 20P (75-150 μm, Mitsubishi, Japan) |

3. Preparation of Extracts and Isolation of Active Ingredients 3.1. Stem Bark of *Alnus Japonica*

The fresh stem barks (5.15 kg) of *Alnus japonica* after harvest were extracted and filtered three times with 80% acetone at room temperature for 24 hrs. The extracted substances (489.77 g) were obtained by concentrating the extract solutions under reduced pressure and suspended in water. After filtration under reduced pressure, Sephadex LH-20 column chromatography on the aqueous portion was carried out. The solvent was increased in a linear gradient from 30% to 100% methanol by every 10% rise and divided into four sub-fractions with the verification with TLC method. MCl-gel CHP 20P column chromatography (0→100% methanol, gradient system) was performed on the fraction 2 (Fr. 2) in which TLC response of oregonin and excellent DPPH activity was demonstrated. Finally, oregonin was extracted and purified in the amount of 39.99 g and its yield rate was 0.78%.

3.2. Leaves of *Alnus Japonica*

The fresh leaves (3 kg) of *Alnus japonica* after harvest were extracted and filtered three times with 80% acetone at room temperature for 24 hrs. The extracted substances (193.59 g) were obtained by concentrating the extract solutions under reduced pressure. After being suspended in water and filtrated under reduced pressure, ethylacetate layer (34.06 g) of the aqueous portion in which oregonin reaction was demonstrated with TLC method was obtained and then, Sephadex LH-20 column chromatography was performed on the ethylacetate fraction. The solvent was increased in a linear gradient from 20% to 100% methanol by every 10% rise and divided into five sub-fractions with the verification by TLC method. MCl-gel CHP 20P column chromatography (0→400% methanol, gradient system) was performed on the fraction 2 (Fr. 2) in which TLC response of oregonin and excellent DPPH activity was demonstrated. Finally, oregonin was produced in the amount of 0.3 g and its yield rate was 0.01%.

4. Chemical Structure Characterization of the Isolated Compound

The isolated oregonin was a form of amorphous powder. MS and NMR data was as follows.

$[\alpha]^{20}_D$: −17.5° (c=1.0, MeOH)

Negative FAB MS: m/z 477 $[M-H]^-$ $^1$H-NMR (300 MHz, Acetone-$d_6$+$D_2O$): δ 6.74-6.71 (4H in total, H-2',2",5',5"), 6.53-6.50 (2H in total, m, H-6",6'), 4.31 (1H, d, J=7.8 Hz, xyl-1), 4.14 (1H, m, H-5), 3.86 (1H, dd, J=11.4, 6.1 Hz xyl-5e), 3.54 (1H, m, xyl-4), 2.83-2.52 (8H in total, H-1,2,4,7), 1.80-1.76 (2H in total, m, H-6)

$^{13}$C-NMR (75 MHz, Acetone-d6+$D_2O$): described in the following Table 2.

In addition, $^{13}$C-NMR of the isolated hirsutenone was described in the following Table 2.

TABLE 2

$^{13}$C-NMR data of hirsutenone and oregonin

| Carbon number | Oregonin | Hirsutenone |
|---|---|---|
| Heptane moiety | | |
| C-1 | 29.7 | 29.9 |
| C-2 | 46.1 | 42.0 |
| C-3 | 210.6 | 210.3 |
| C-4 | 48.2 | 131.1 |
| C-5 | 76.1 | 147.5 |
| C-6 | 38.3 | 34.8 |
| C-7 | 31.4 | 34.0 |
| Diphenyl moiety | | |
| C-1' | 133.9 | 133.4 |
| C-1" | 134.9 | 133.7 |
| C-2' | 116.1 | 115.9 |
| C-2" | 116.2 | 116.0 |
| C-3' | 145.9 | 145.6 |
| C-3" | 145.9 | 145.6 |
| C-4' | 144.0 | 143.8 |
| C-4" | 144.3 | 143.9 |
| C-5' | 116.4 | 116.1 |
| C-5" | 116.5 | 116.1 |
| C-6' | 120.5 | 120.3 |
| C-6" | 120.4 | 120.2 |
| Sugar moiety | | |
| C-1 | 104.0 | |
| C-2 | 74.6 | |
| C-3 | 77.5 | |
| C-4 | 70.8 | |
| C-5 | 66.6 | |
| C-6 | (xyl) | |

* 75 MHZ (Acetone-$d_6$ + $D_2O$)

Figure 2A:
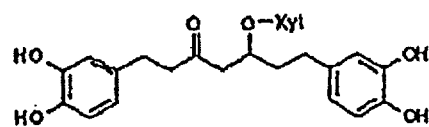
FIG. 2a represents $^1$H-NMR and $^{13}$C-NMR spectra of oregonin purified from the stem bark of *Alnus japonica*.
Figure 2A:
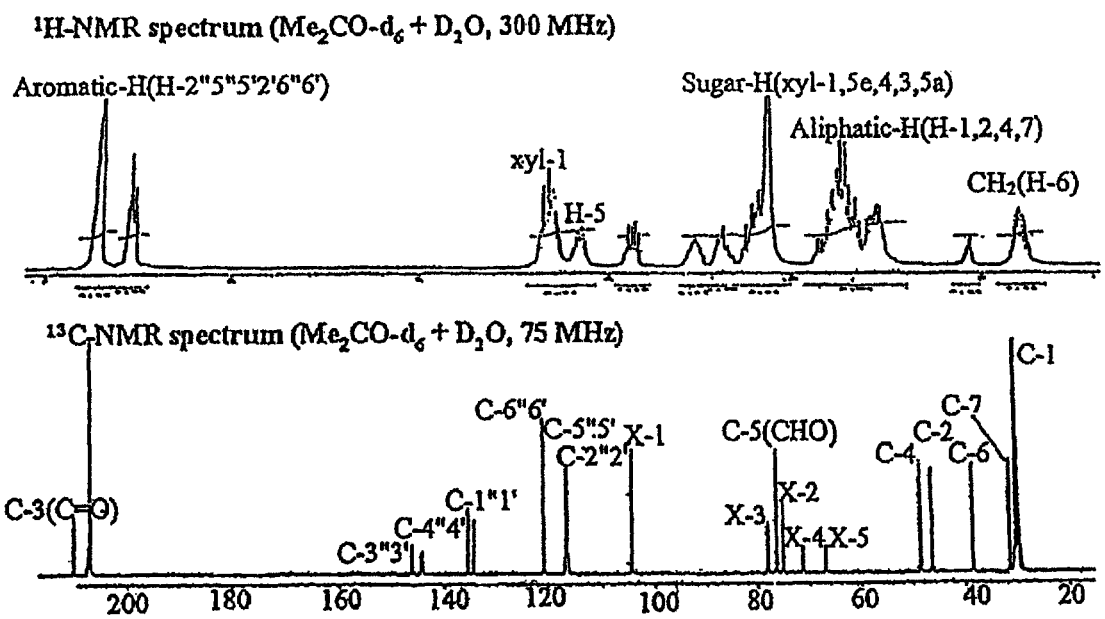
Figure 2B:
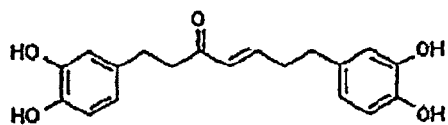
FIG. 2b represents $^1$H-NMR and $^{13}$C-NMR spectra of hirsutenone purified from the stem bark of *Alnus japonica*.
Figure 2B:
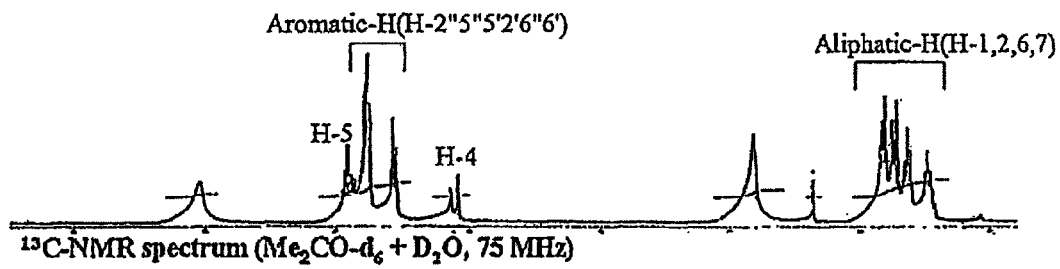
Figure 2B:
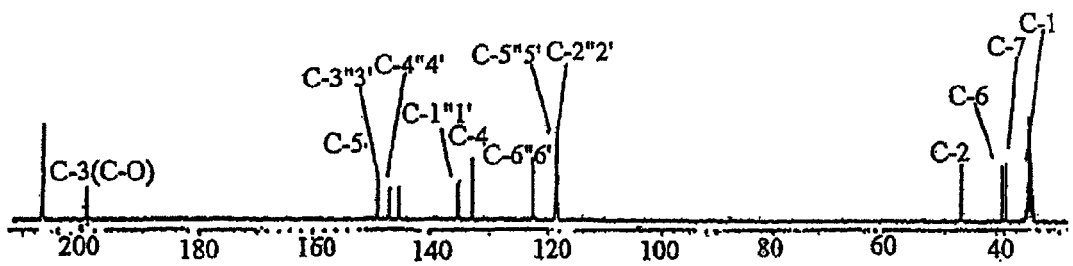

$^1$H-NMR and $^{13}$C-NMR spectra of oregonin and hirsutenone were represented in FIG. 2a and in FIG. 2b, respectively.

NMR and MS data of oregonin and hirsutenone were consistent with the reference, identifying their structure.

5. Preparation of Hirsutenone Using Enzymatic Hydrolysis of Oregonin

Figure 3B:
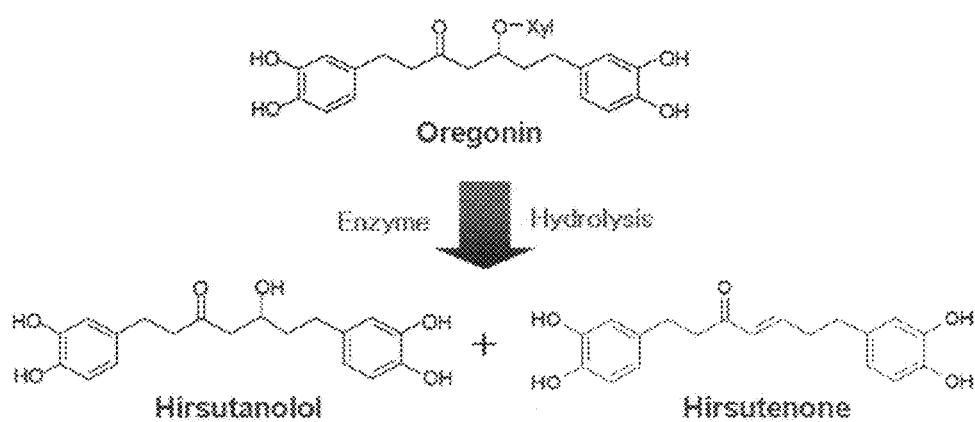

A large amount of oregonin, a form of glycoside occupied in the extracts of the stem barks and leaves of *Alnus japonica*, and hirsutenone and hirsutenonol as aglycones was included in a small amount. Hirsutenone and hirsutanonol was massively produced by hydrolysis of oregonin using an enzyme. The enzymes used were Pectinex 5XL, Fungamyl AX and Pectinex AFP L4 (Nobozyme, Co.). The practical procedures and methods of enzymatic hydrolysis were shown in FIGS. 3a-3c. As results, hirsutanonol and hirsutenone compounds (aglycones) were simultaneously obtained from oregonin (glycoside). Two aglycone compounds (hirsutanonol and hirsutenone) were independently separated using Sephadex LH-20 column chromatography (60% MeOH Isocratic).

The result of enzymatic hydrolysis was represented in Table 3.

TABLE 3

Enzymatic Hydrolysis

| Kind of enzyme | Enzyme contents (%) | Ore main Fr. (g) | Enzymatic hydrolysis products (g) | Yield (%) |
|---|---|---|---|---|
| Pectinex 5XL | 10 | 1 | 0.38 | 38 |
| Fungamyl AX | 10 | 2 | 1.53 | 76.5 |
| Pectinex AFP L4 | 3 | 1 | 0.49 | 49 |
| Pectinex AFP L4 | 5 | 1 | 0.63 | 63 |

Figure 4:
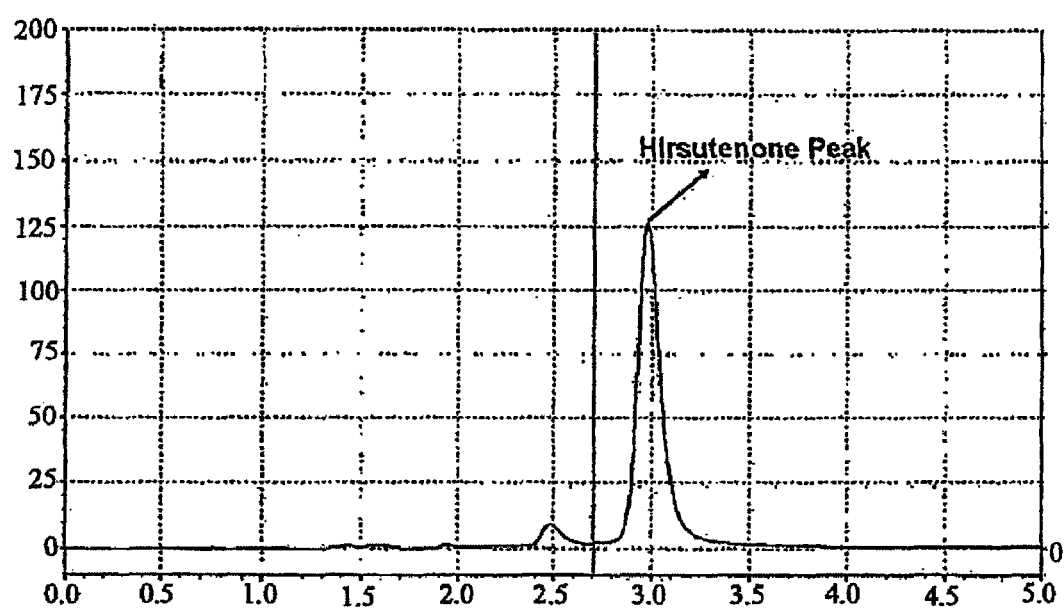
FIG. 4 represents results of a HPLC (high performance liquid chromatography) on hirsutenone.

6. Preparation of Formulation Containing Hirsutenone 6.1. HPLC Assay Condition and Calibration Curve Method The stock solution (100 μg/ml) of hirsutenone purified from the stem bark of *Alnus japonica* was prepared by dissolving in methanol and the standard solutions at concentrations of 1, 5, 10, 25, 50 μg/ml were fabricated by diluting the stock solution. The mixture of acetonitrile and distilled water (70:30 v/v) was used for the mobile phase. Detection wavelength, injection volume and flow rate was 280 nm, 20 μl and 1 ml/min respectively. The retention time of hirsutenone was 3 min under the above conditions. In HPLC assay, calibration curve based on each concentration and peak area was made and represented in suitable linearity ($R^2$=0.997) at a range of concentration of 1-50 μg/ml. HPLC assay of hirsutenone was shown in FIG. 4.

6.2. Preparation of Injection Formulation Containing Hirsutenone

For evaluation of hirsutenone efficacy through injection, the aqueous injection formulations containing 0.1% or 1% (w/v) hirsutenone were prepared according to the compositions of the following Table 4. Each 10 and 100 mg of hirsutenone was weighed and dissolved in suitable amounts of sterilized distilled water containing 10% ethanol for injection. The pH of these solutions was adjusted to between pH 6.5 and pH 7.4 by adding small amount of NaOH solution and then fabricated to pH 10 by adding sterilized distilled water for injection. Formulation of drugs was determined using HPLC.

TABLE 4

Composition for Hirsutenone Injection

| Ingredients | Formulation (%) |
|---|---|
| Hirsutenone | 0.1-1.0 |
| NaOH | q.s. |
| Ethanol | 10 |
| Water for injection | q.s. |
| Total | 100 |

6.3. Preparation of Ointment Formulation Containing Hirsutenone

Formulation of hirsutenone was fixed in 1% (w/w). O/W (oil-in-water) cream ointment was prepared according to the following method. The compositions of O/W cream were formulated according to component ratio of Table 5. Polyglyceryl-3-methylglucose distearate, stearic acid, cetyl alcohol, paraffin liquid and hirsutenone were mixed depending on composition and were formulated as oil phase by heating at 65° C. On the other hand, glycerin and distilled water were completely mixed by heating at 65° C., finally formulated as the aqueous phase. Oil solution was added to water solution and emulsified for several min using a homogenizer. After cooling, O/W cream was formulated.

TABLE 5

Composition of Hirsutenone Ointment Formulation

| Ingredients | Formulation (%) |
|---|---|
| Polyglyceryl-3 methylglucose distearate | 3 |
| Stearic acid | 5 |
| Cetyl alcohol | 2 |
| Mineral oil | 7 |
| Glycerin | 10 |
| Water | 73 |

7. Animal Model for Atopic Dermatitis 7.1. Mite Patch

To examine treatment efficacy of hirsutenone on atopic dermatitis, the present inventors utilized an experimental animal model in which atopic dermatitis was induced by attachment of mite patch to the skin. Briefly, the patch containing a mite-derived ingredient as a human atopic dermatitis-inducing agent was applied to 5-old-week mice. The hairs of their back were partially removed and mite patch was attached. At 2-week post-application, skin damage equivalent to atopic dermatitis was observed. Mite patch was detached at 18 weeks.

7.2. NC/Nga Mouse

To research treatment efficacy of hirsutenone on atopic dermatitis, the present inventors also utilized NC/Nga mouse, an animal model known to those skilled in the art (Vestergaard C, Yoneyama H, Murai M, Nakamura K, Tamaki K, Terashima Y, Imai T, Yoshie O, Irimura T, Mizutani H and Matsushima K. Overproduction of Th2-specific chemokines in NC/Nga mice exhibiting atopic dermatitis-like lesions, *J Clin Invest*, 104 (8): 1097-105 (1999)). In addition to NC/Nga mouse, BABL/c mouse was used as an animal model.

8. Eosinophil Count

Mouse blood was collected into capillary tube and 30 μl of mouse whole blood was diluted 6-fold by addition of 150 μl saline. Eosinophils were counted using a Sysmex XE-2100 hematology analyzer. Slide glass smeared with peripheral blood was prepared and stained with Wright-Giemsa. Eosinophil count was carried out by differentially counting 200 leukocytes.

9. ELISA Measurement

Serum was prepared from blood of main artery. Lymphocytes extracted from spleen were cultured. Briefly, extracted spleen was homogenized, filtered through mesh and single cells was isolated. Red blood cells were lysed in RBC lysis buffer and the supernatant was removed by centrifugation. $1\times10^6$ cells were cultured in 24-well plate containing RPMI media (1 ml). The experiments were performed in media containing cells cultured for 3 days.

10. Real-time PCR

The primers used in Real-time PCR are as follows.

TABLE 6

Primer Sequences

| Primer | Sequence | |
|---|---|---|
| MBD-1 (362bp) | 5'-ACATAAAGGACGAGCGATGG-3' | (sense) |
| | 5'-TGCAGATGGGGTGTCATAGA-3' | (anti-sense) |
| MBD-2 (199bp) | 5'-GCCATGAGGACTCTCTGCTC-3' | (sense) |
| | 5'-AGG GGT TCT TCT CTG GGA AA-3 | (anti-sense) |
| MBD-3 (169bp) | 5'-TCA GAT TGG CAG TTG TGG AG-3' | (sense) |
| | 5'-GCT AGG GAG CAC TTG TTT GC-3' | (anti-sense) |
| iNOS (203bp) | 5'-CTG ATG CCT CTT CCA GGT GT-3' | (sense) |
| | 5'-GAG GGA GCC CTT TCT GAA TC-3' | (anti-sense) |
| COX-2 (593bp) | 5'-CCA CCC ATG GCA AAT TCC ATG GCA-3' | (sense) |
| | 5'-GGTGCTGCTTGTTAGGAGGTCAAGTAAAGGGC-3' | (anti-sense) |
| GAPDH (598bp) | 5'-CCA CCC ATG GCA AAT TCC ATG GCA-3' | (sense) |
| | 5'-CCC TGT TGC TGT AGC CGT AT-3' | (anti-sense) |

Total RNA was extracted according to the following steps. Tissue was treated with 1 ml TRIZol reagent and mixed with 200 µl chloroform. After centrifugation at 12,000 rpm for 15 min at 4° C., the supernatant was transferred into a new tube and mixed with ½ vol. of isopropanol. The mixture was again centrifuged at 12,000 rpm for 15 min at 4° C. The supernatant was discarded and total RNA was dissolved in DEPC-water.

cDNA was prepared according to the following steps. The isolated total RNA was dissolved in 30 µl DEPC-DW and reverse transcription using 3 µg of total RNA as a template was performed in a reaction mixture (20 µl) containing 1 µl of reverse transcriptase, 2 µl of 10× buffer, 2 µl of 10 mM dNTP (dNTP mix), 1 µl of oligo dT primer, 0.5 µl of RNase inhibitor and 4 µl of 25 mM $MgCl_2$.

Each 2 µl of cDNA prepared was amplified using PCR. PCR reaction was performed by 45 cycles of 1 min at 59° C. and 1 min at 94° C. Finally, the mixtures were incubated at 72° C. for 1 min for extension.

11. Western Blotting

Skin tissue containing epidermal cells was lysed and centrifuged using a centrifuge. The supernatant was electrophoresized on 15% SDS-PAGE (sodium dodecyl sulfate polyacrylamide gel electrophoresis). For analysis of COX-2 and iNOS, proteins separated on gel electrophoresis were transferred into a nitrocellulose membrane and sequentially incubated with a primary antibody (1:1000 in BSA, rabbit polyclonal anti-COX-2 antibody, rabbit polyclonal iNOS antibody; Chemicon, Calif., USA) and a secondary antibody (1:2000 in BSA, anti-goat IgG, anti-rabbit IgG; Chemicon, Calif., USA).

Experimental Results

1. Naked-Eye Observation of Atopic Dermatitis in Animal Model

Figure 5A:
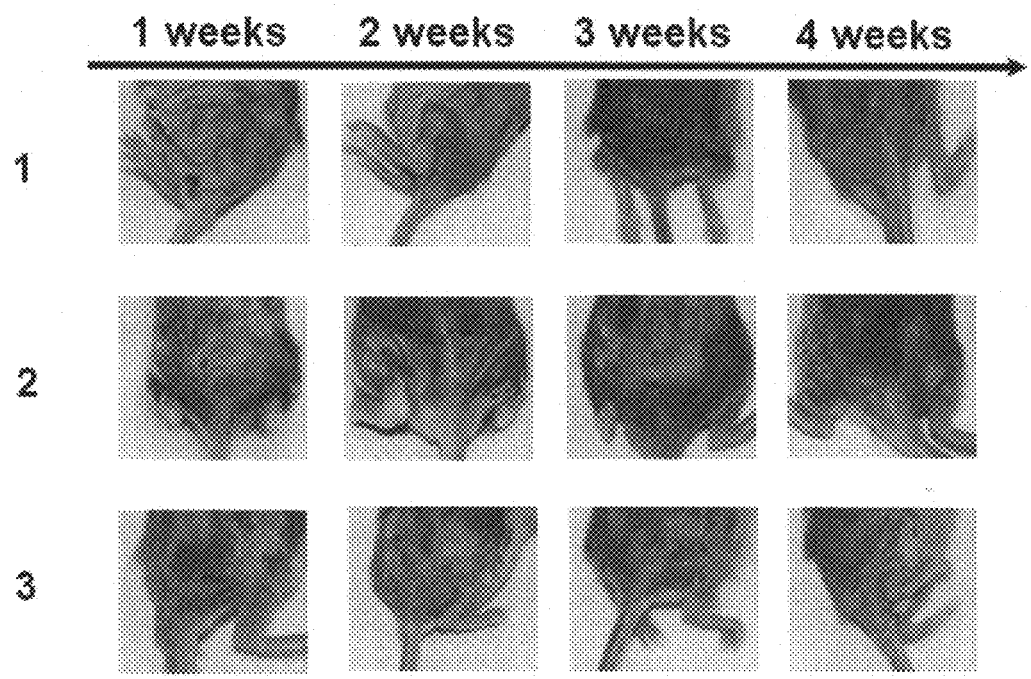
FIG. 5a is photographs showing treatment effect on atopic dermatitis after PBS was injected into NC/Nga mouse in which the atopic dermatitis had been induced as a negative control.
Figure 5B:
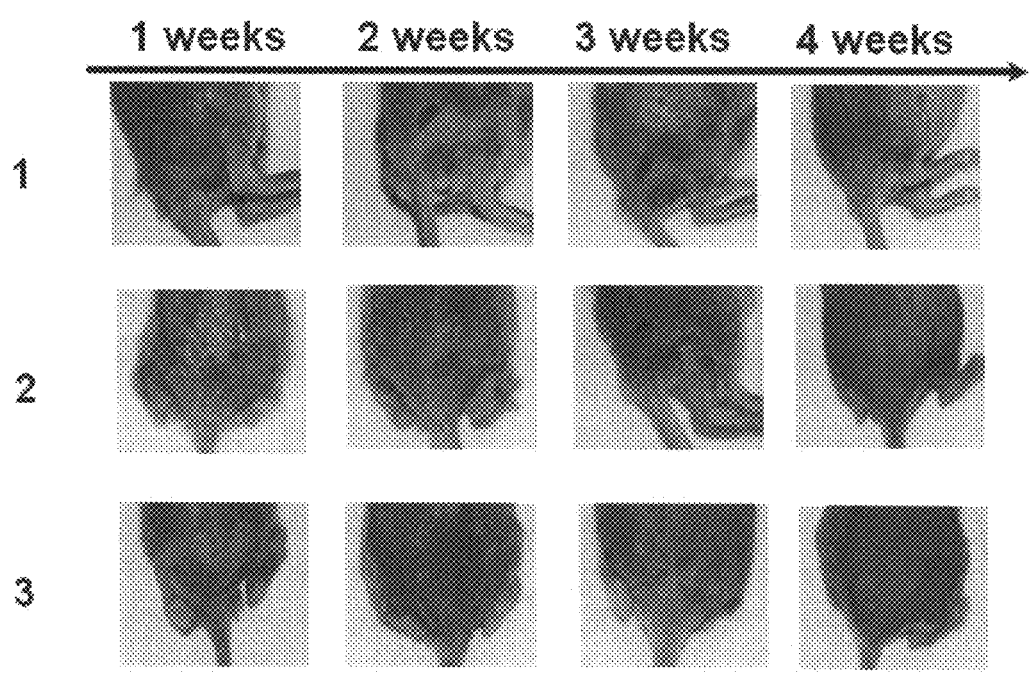
FIG. 5b is photographs showing treatment effect on atopic dermatitis after 0.1% hirsutenone was injected into NC/Nga mouse in which the atopic dermatitis had been induced.
Figure 5C:
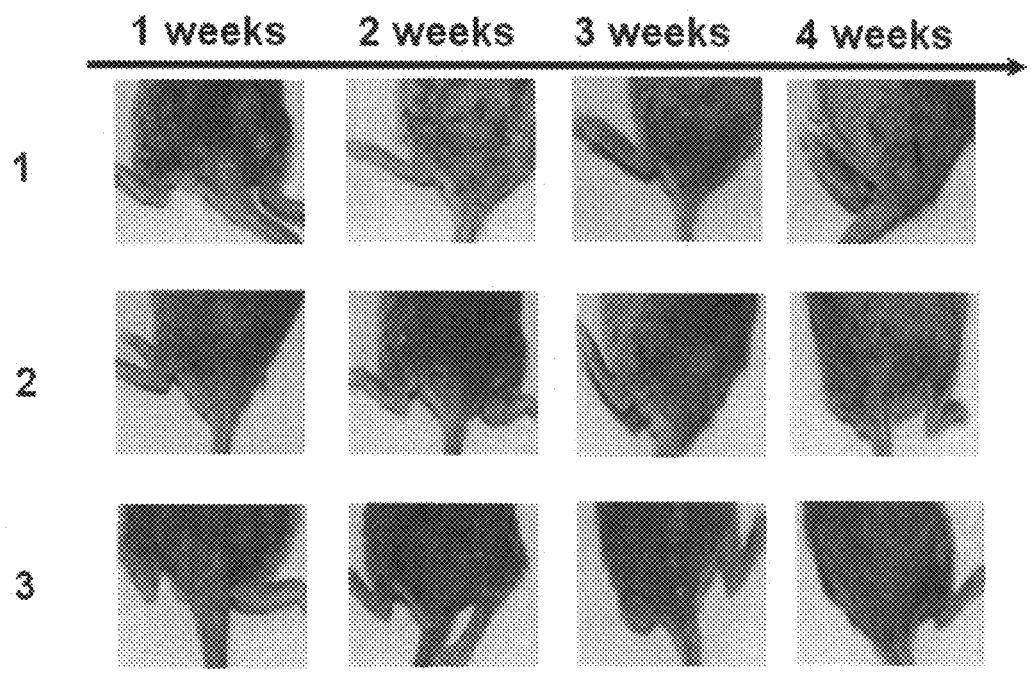
FIG. 5c is photographs showing treatment effect on atopic dermatitis after 1% hirsutenone was injected into NC/Nga mouse in which the atopic dermatitis had been induced.
Figure 5D:
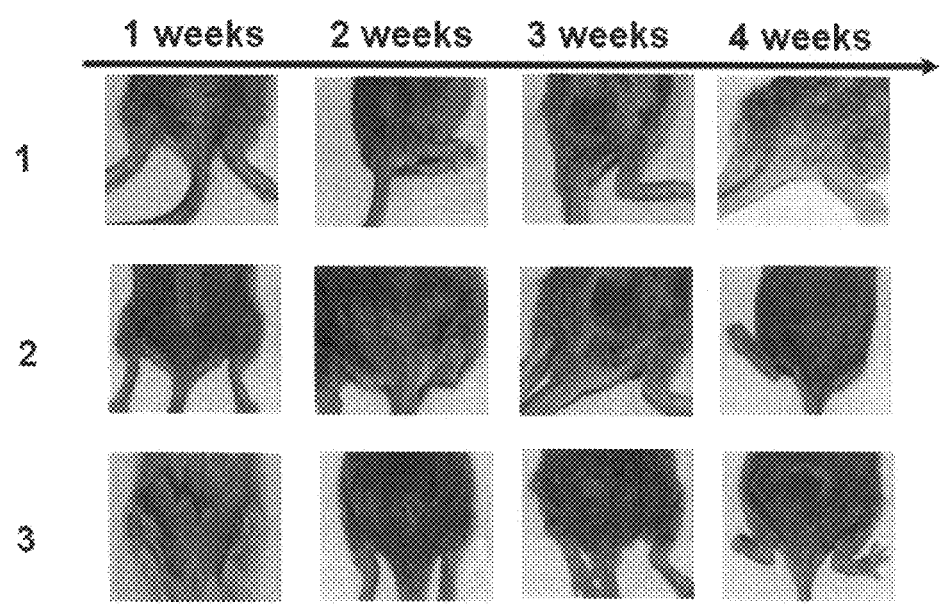
FIG. 5d is photographs showing treatment effect on atopic dermatitis after dexamethasone was injected into NC/Nga mouse in which the atopic dermatitis had been induced as a positive control.
Figure 5E:
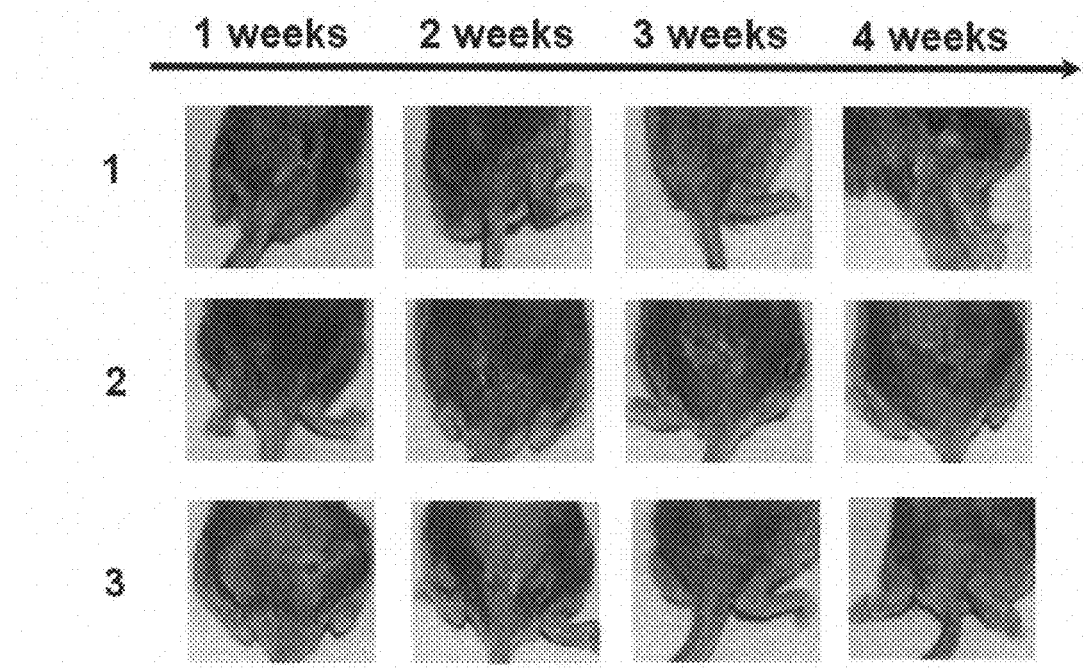
FIG. 5e is photographs showing treatment effect on atopic dermatitis after a composition without an active ingredient (baseline) was applied to the skin of NC/Nga mouse in which the atopic dermatitis had been induced as negative control.
Figure 5G:
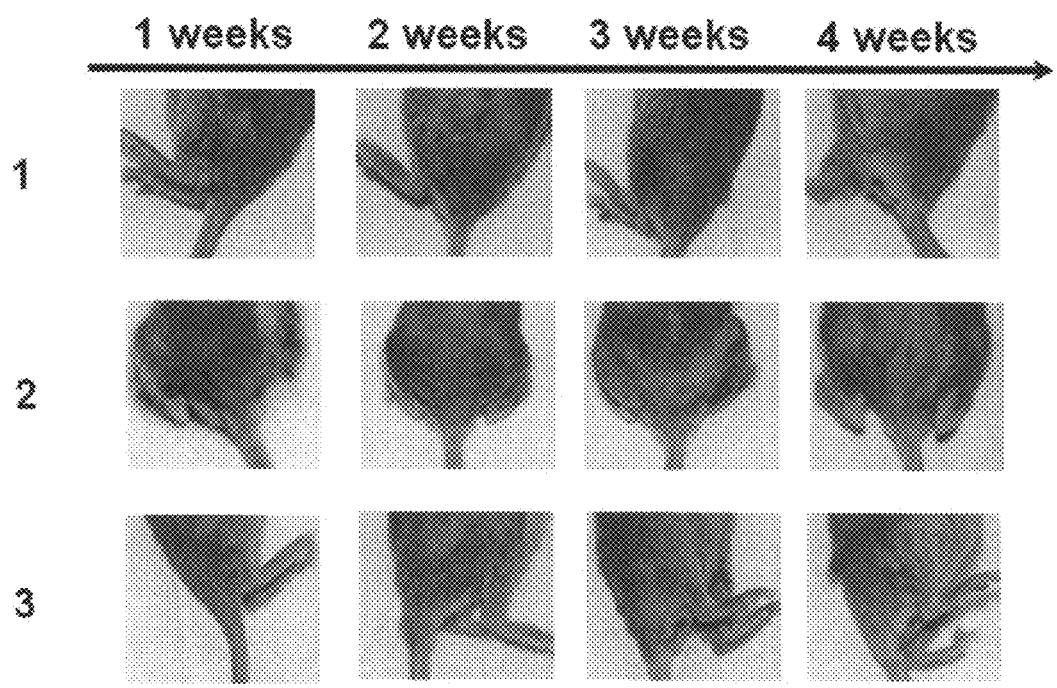
FIG. 5g is photographs showing treatment effect on atopic dermatitis after plancol was applied to the skin of NC/Nga mouse in which the atopic dermatitis had been induced as a positive control.

To examine treatment efficacy of hirsutenone on atopic dermatitis, mice in which atopic dermatitis had been induced were treated with hirsutenone through an injection or skin application for 4 weeks. Then, external skin morphology was estimated by naked-eye observation so as to determine whether a symptom of atopic dermatitis was relieved. Each group injected or applied with hirsutenone was compared to a negative control group into which hirsutenone was not administered, resulting in the improvement of a symptom of atopic dermatitis. Specifically, it was demonstrated that a symptom of atopic dermatitis was much more improved in NC/Nga mice group in which 0.1% and 1% hirsutenone (each FIG. 5b and FIG. 5c) was administered by an injection than in mice in which PBS (FIG. 5a) was administered as a negative control. FIG. 5d represents a positive control treated with dexamethasone. In addition, it was demonstrated that a symptom of atopic dermatitis was much more remarkably improved in mice in which 1% hirsutenone (FIG. 5f) ointment was applied to the skin compared to a negative control treated with composition not containing any active ingredient (FIG. 5e). FIG. 5g represents the result of administration of plancol as positive control.

Figure 6A:
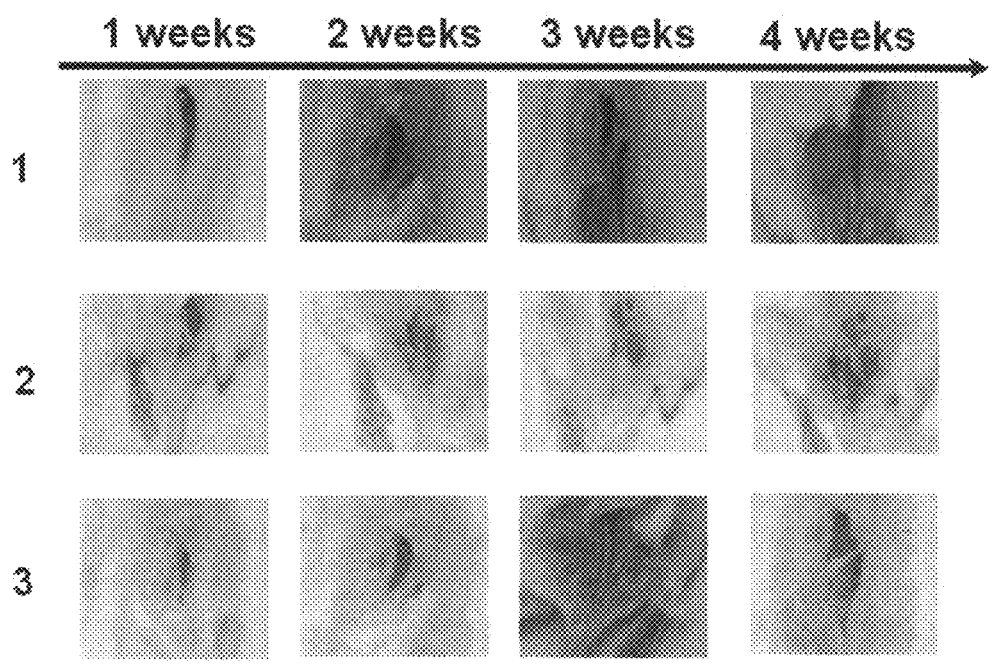
FIG. 6a is photographs showing treatment effect on atopic dermatitis after PBS was injected into BALB/c mouse in which the atopic dermatitis had been induced as negative control.
Figure 6B:
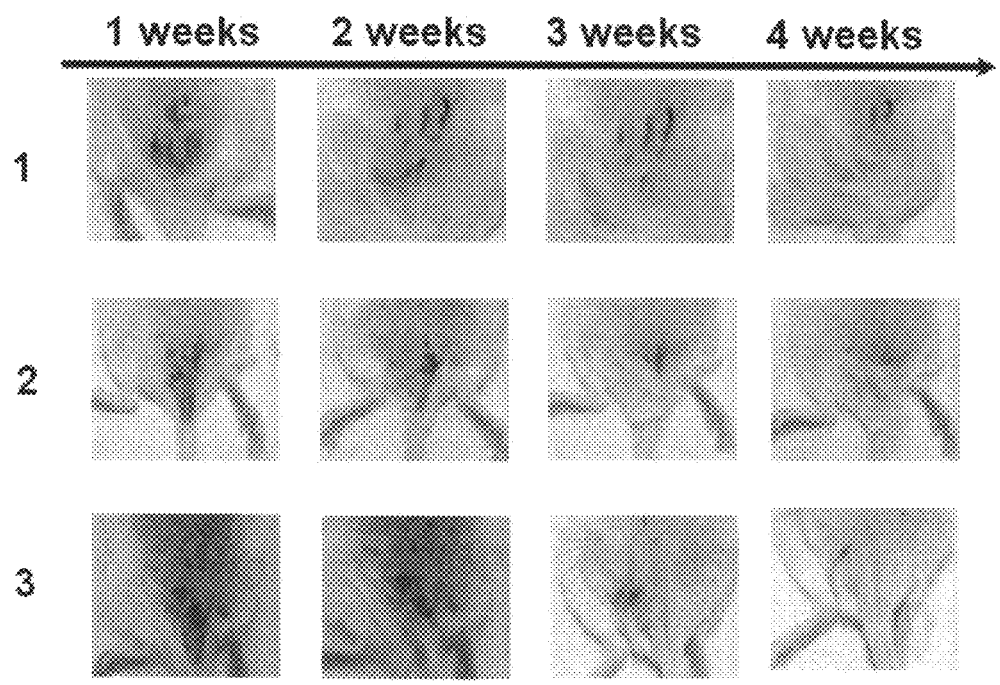
FIG. 6b is photographs showing treatment effect on atopic dermatitis after 0.1% hirsutenone was injected into BALB/c mouse in which the atopic dermatitis had been induced.
Figure 6C:
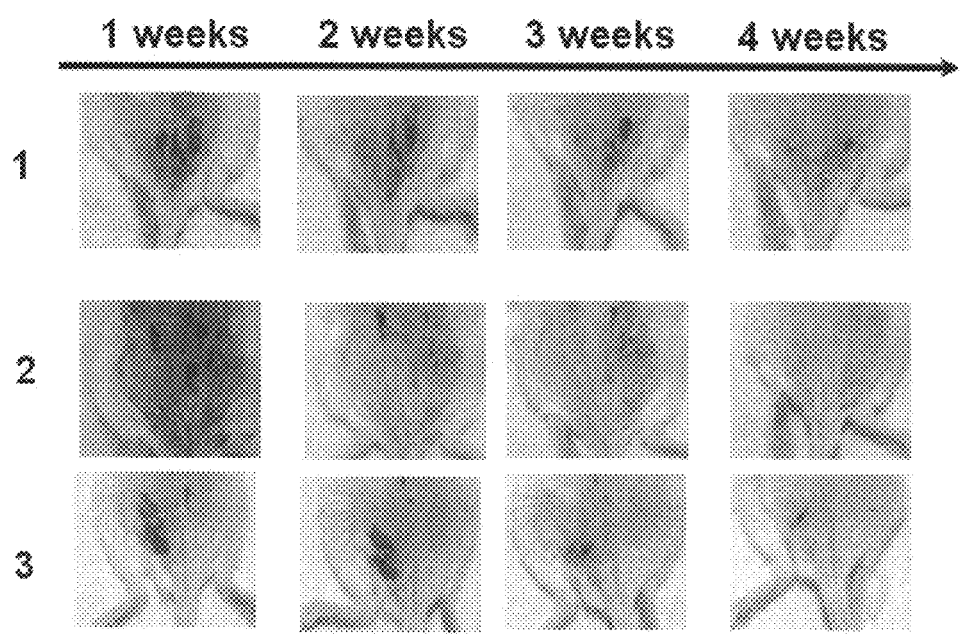
FIG. 6c is photographs showing treatment effect on atopic dermatitis after 1% hirsutenone was injected into BALB/c mouse in which the atopic dermatitis had been induced.
Figure 6E:
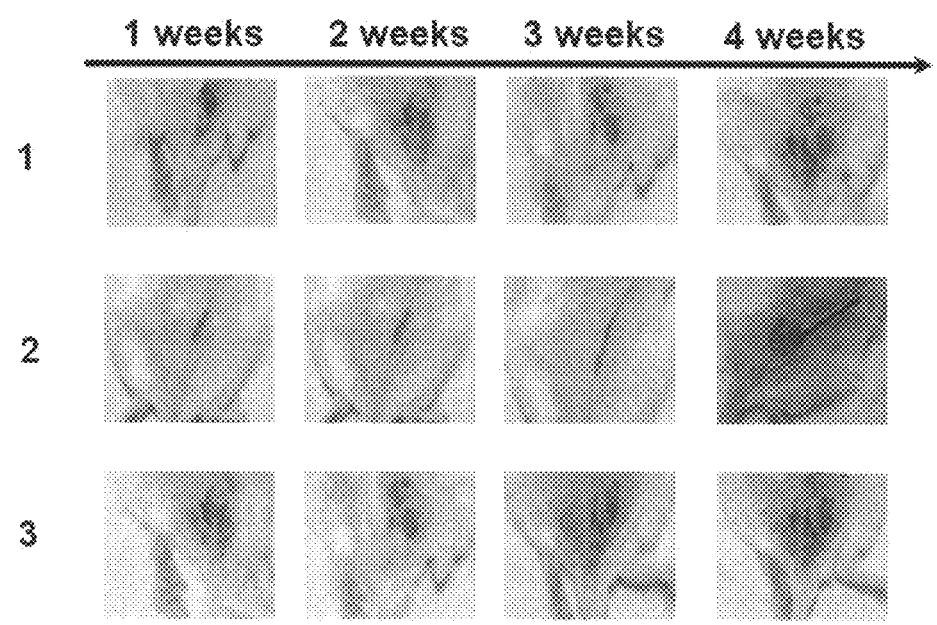
FIG. 6e is photographs showing treatment effect on atopic dermatitis after a composition without the active ingredient (baseline) was applied to the skin of BALB/c mouse in which the atopic dermatitis had been induced as negative control.
Figure 6F:
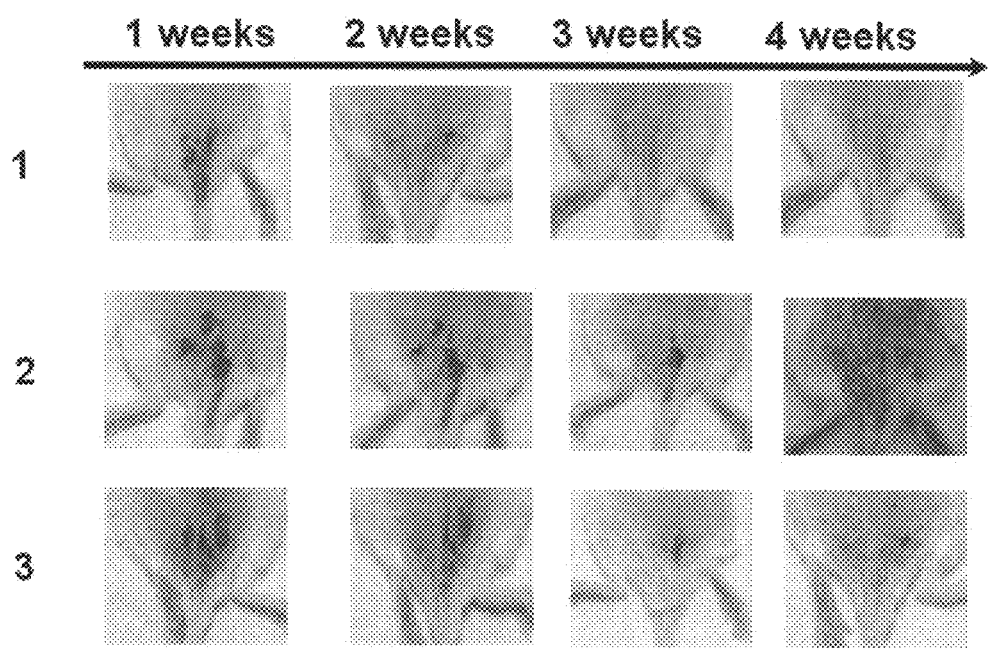
FIG. 6f is photographs showing treatment effect on atopic dermatitis after 1% hirsutenone applied to the skin of BALB/c mouse in which the atopic dermatitis had been induced.
Figure 6G:
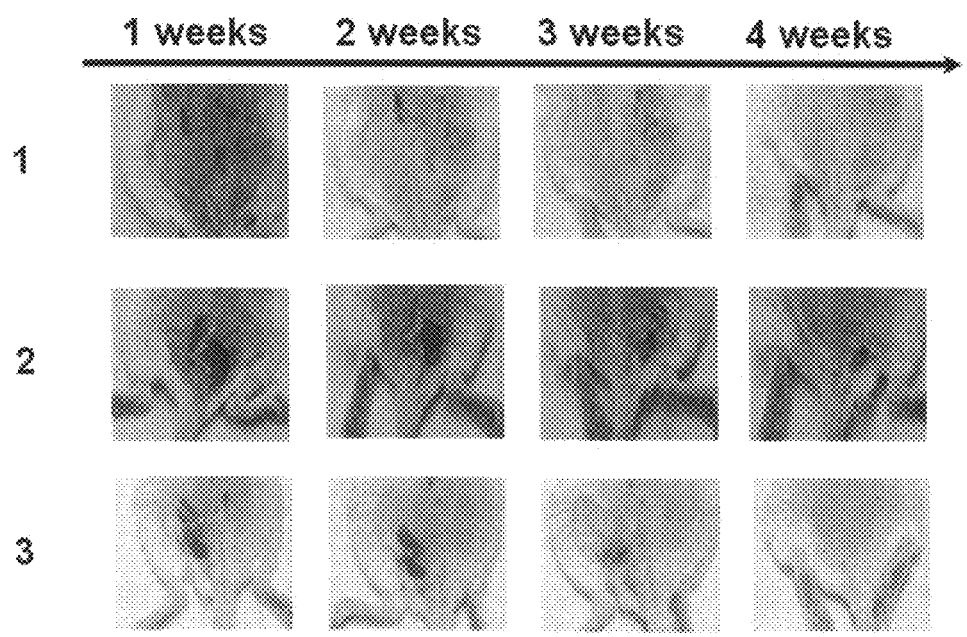
FIG. 6g is photographs showing treatment effect on atopic dermatitis after plancol was applied to the skin of BALB/c mouse in which the atopic dermatitis had been induced as positive control.

Furthermore, it was demonstrated that a symptom of atopic dermatitis was much more relieved in BABL/c mice in which atopic dermatitis had been induced when treated with 0.1% or 1% hirsutenone (each FIG. 6b and FIG. 6c) by injection compared to a negative control treated with PBS (FIG. 6a). FIG. 6d represents a positive control treated with dexamethasone. In addition, it was demonstrated that a symptom of atopic dermatitis was much more alleviated in mice when 1% hirsutenone ointment (FIG. 6f) was applied to skin compared to a negative control treated with composition not containing any active ingredient (FIG. 6e). FIG. 6g represents the result of administration of plancol as positive control.

2. Eosinophil Count

Figure 7A:
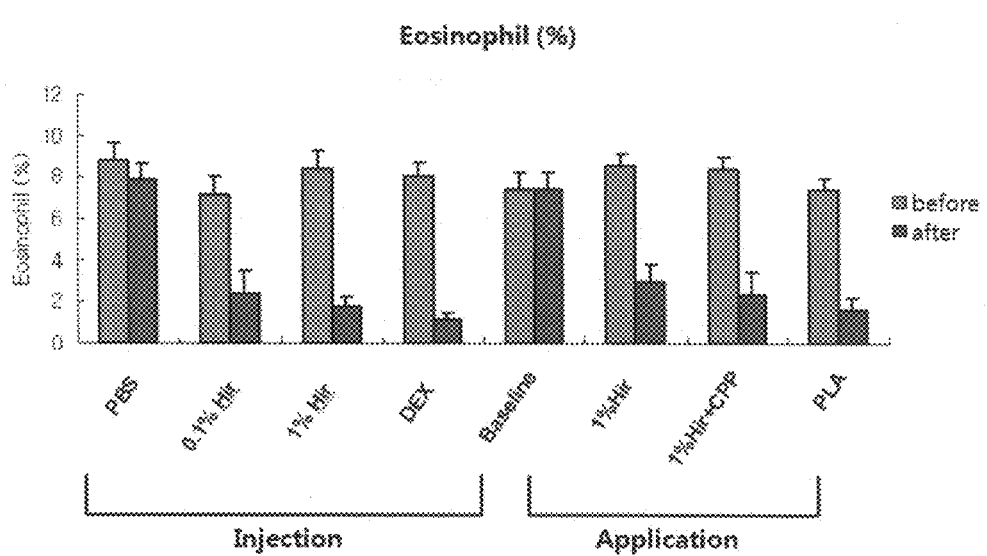
FIGS. 7a and 7b are graphs showing the ratio and number of eosinophil in the blood samples obtained from each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.
Figure 7B:
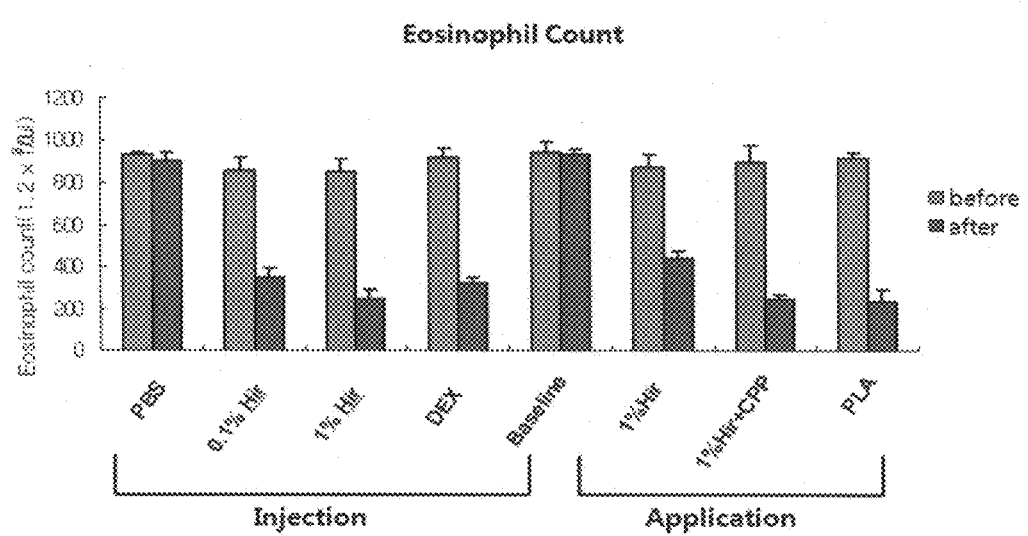
Figure 7C:
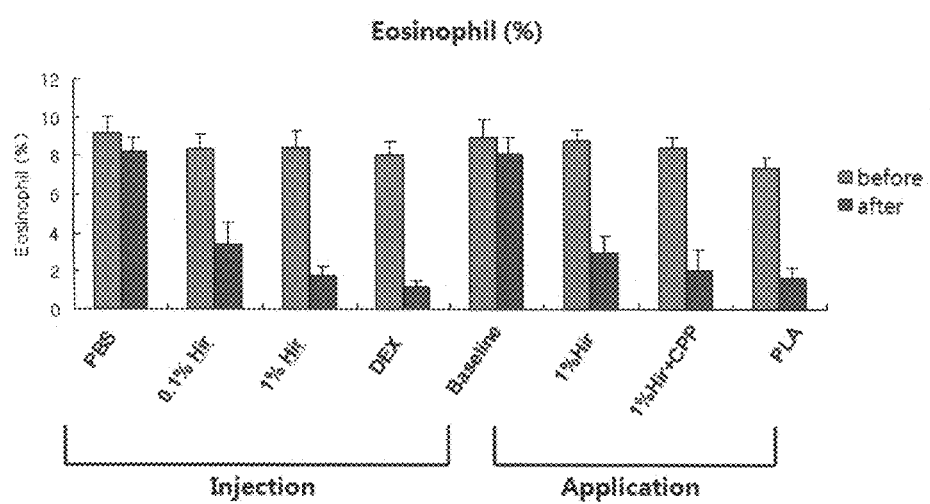
FIGS. 7c and 7d are graphs showing the ratio and number of eosinophil in the blood samples obtained from each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.
Figure 7D:
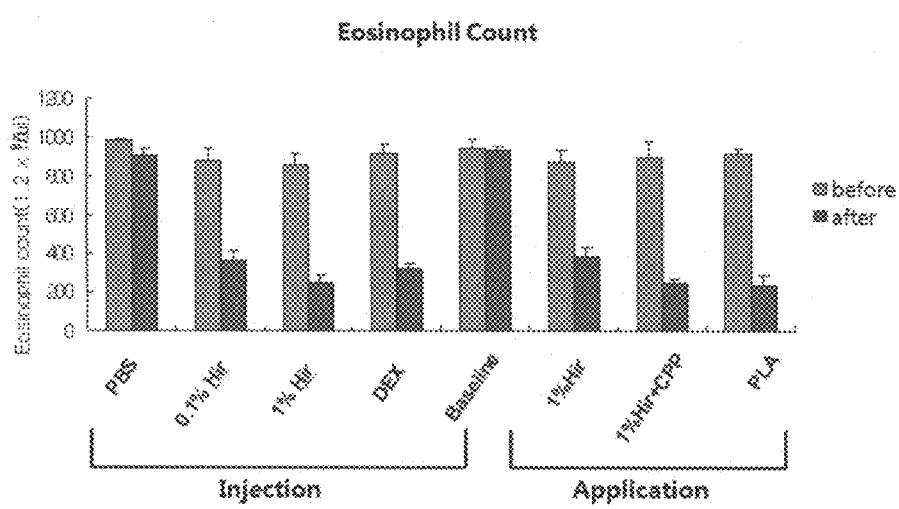

NC/Nga mice in which atopic dermatitis had been induced were treated with hirsutenone through an injection or skin application for 4 weeks. Blood was collected from mice before and after administration or application of hirsutenone, and then eosinophil count was measured. It was demonstrated that the number of eosinophil after administration or application of hirsutenone was more severely reduced than those measured before administration or application of hirsutenone (FIGS. 7a-7b). In addition, similar results in BABL/c mice in which atopic dermatitis has been induced were obtained (FIGS. 7c-7d).

3. Measurement of IgE Level

Figure 8A:
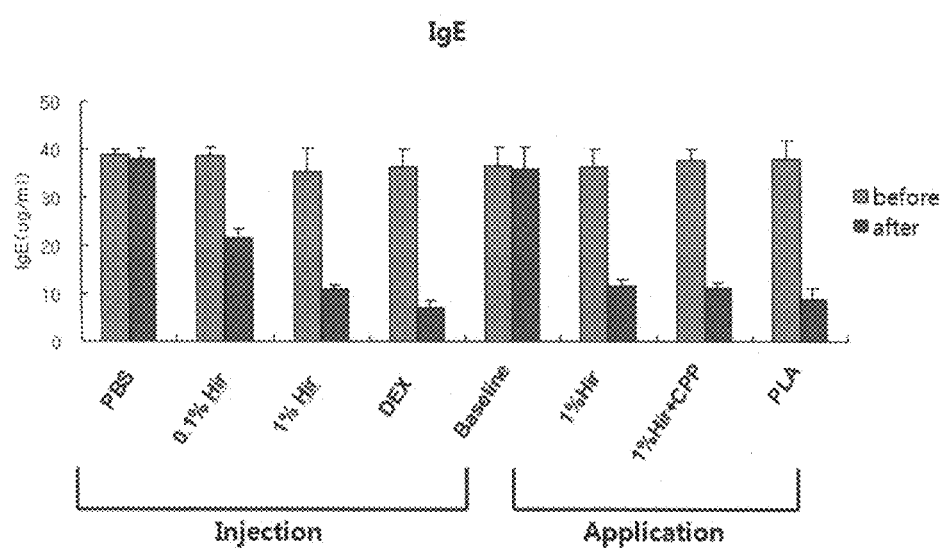
FIG. 8a is a graph showing IgE level measured by ELISA in the blood samples obtained from each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.
Figure 8B:
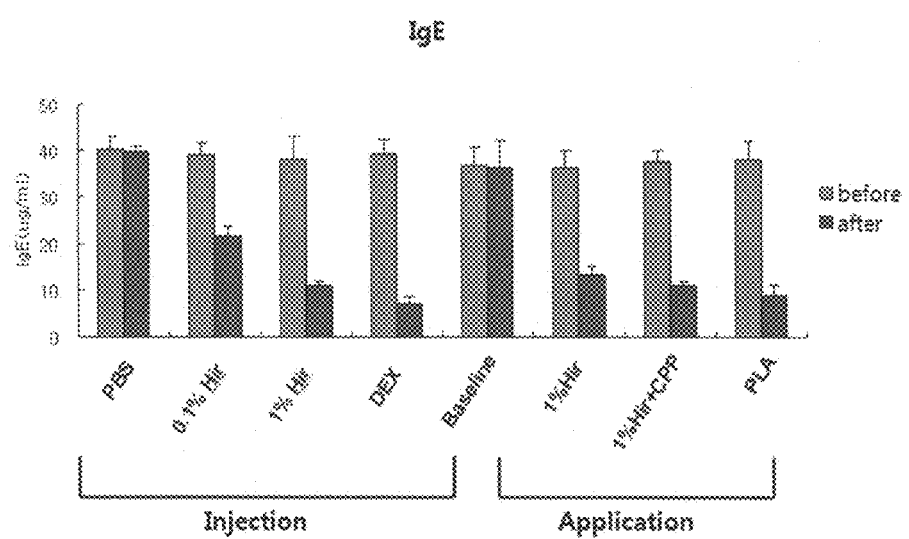
FIG. 8b is a graph showing IgE level measured by ELISA in the blood samples obtained from each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.

NC/Nga mice in which atopic dermatitis had been induced were treated with hirsutenone through an injection or skin application for 4 weeks. Blood was collected from mice and IgE expression level was measured using ELISA. IgE expression detected in groups of hirsutenone being injected or skin applied was remarkably lower than those of negative control (FIG. 8a). In addition, similar results in BABL/c mice in which atopic dermatitis has been induced were obtained (FIG. 8b).

4. Measurement of Interleukin (IL)-4, IL-5 and IL-13 Expression Level

Figure 9B:
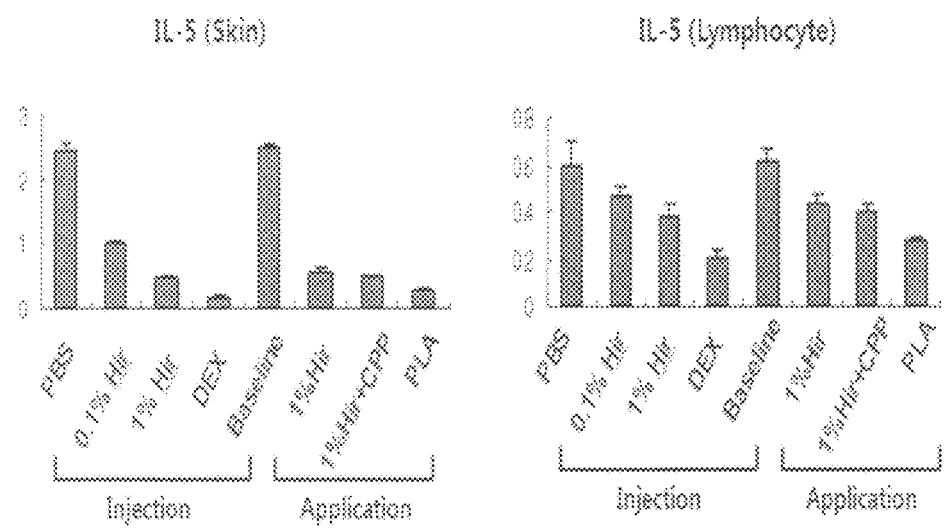
FIG. 9b is a graph showing IL-5 level measured by ELISA in the skin and lymph node obtained from each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.
Figure 9C:
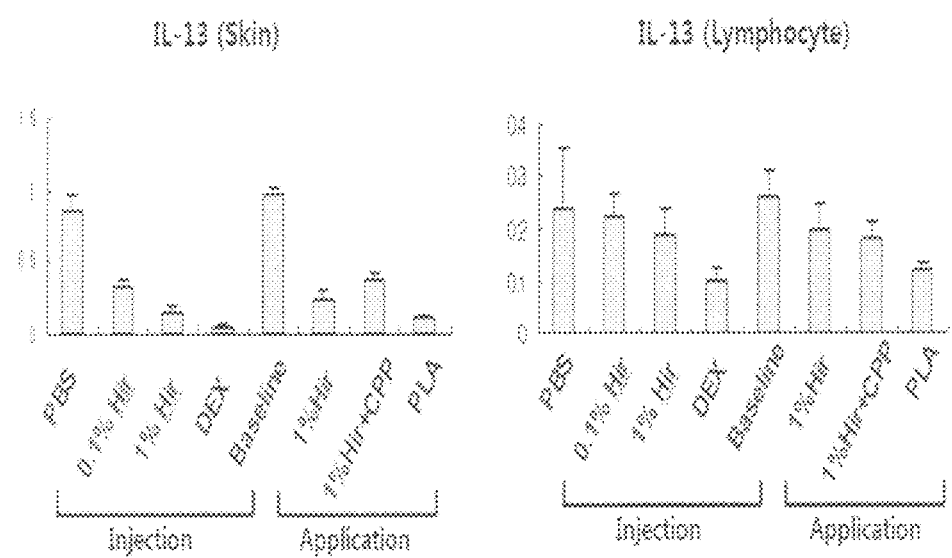
FIG. 9c is a graph showing IL-13 level measured by ELISA in the skin and lymph node obtained from each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.

NC/Nga mice in which atopic dermatitis had been induced were treated with hirsutenone through an injection or skin application for 4 weeks. Blood and spleen were collected from mice and interleukin (IL)-4, IL-5, IL-10 and IL-13 expression level in serum and splenocyte were measured using ELISA. IL-4, IL-5 and IL-13 expression detected in groups of hirsutenone being injected or skin applied was much lower than those of negative control (FIG. 9a, FIG. 9b and FIG. 9c).

Figure 9D:
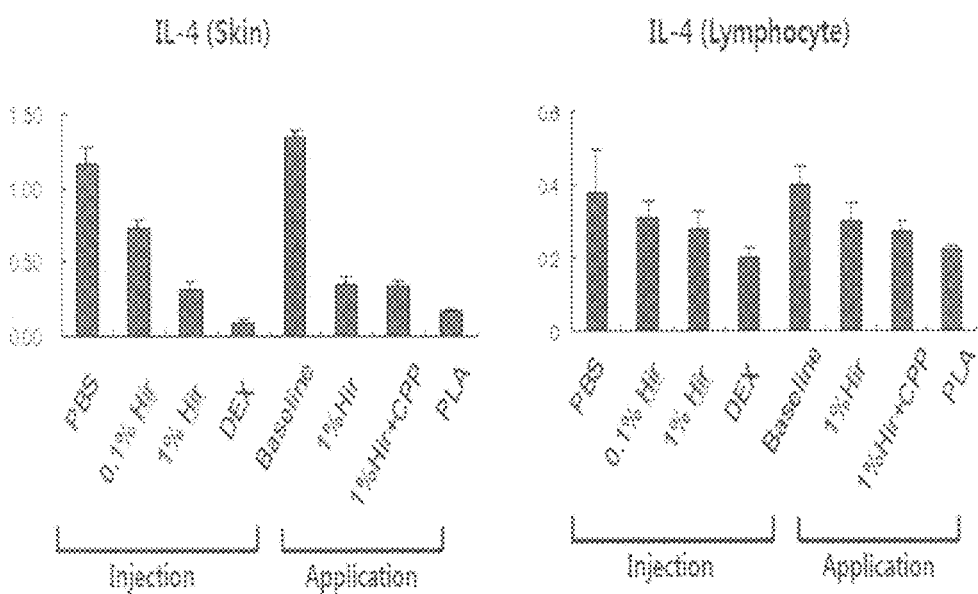
FIG. 9d is a graph showing IL-4 level measured in the skin and lymph node obtained from each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.
Figure 9E:
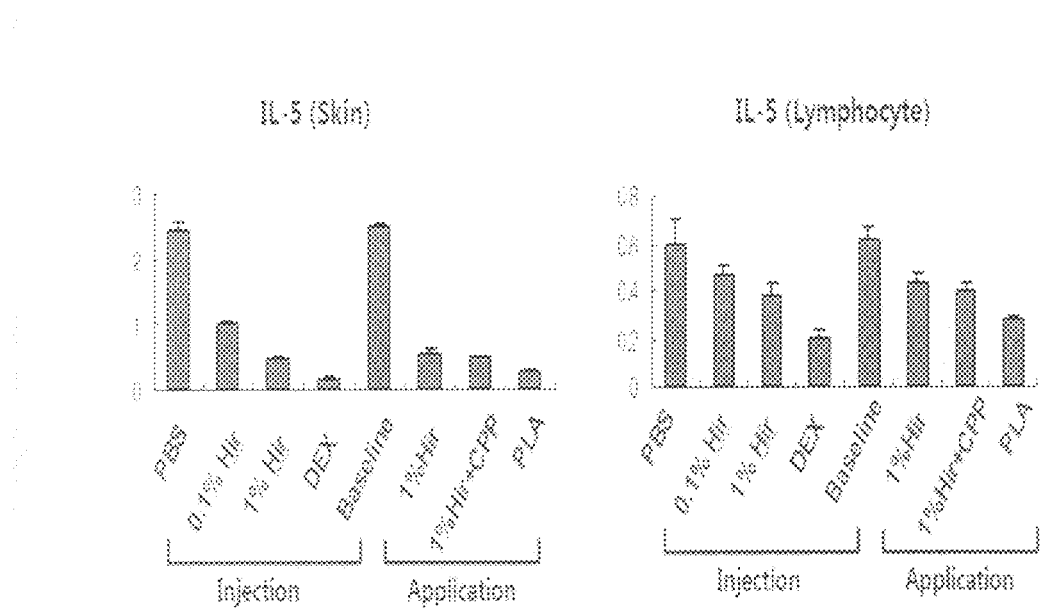
FIG. 9e is a graph showing IL-5 level measured by ELISA in the skin and lymph node from each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.
Figure 9F:
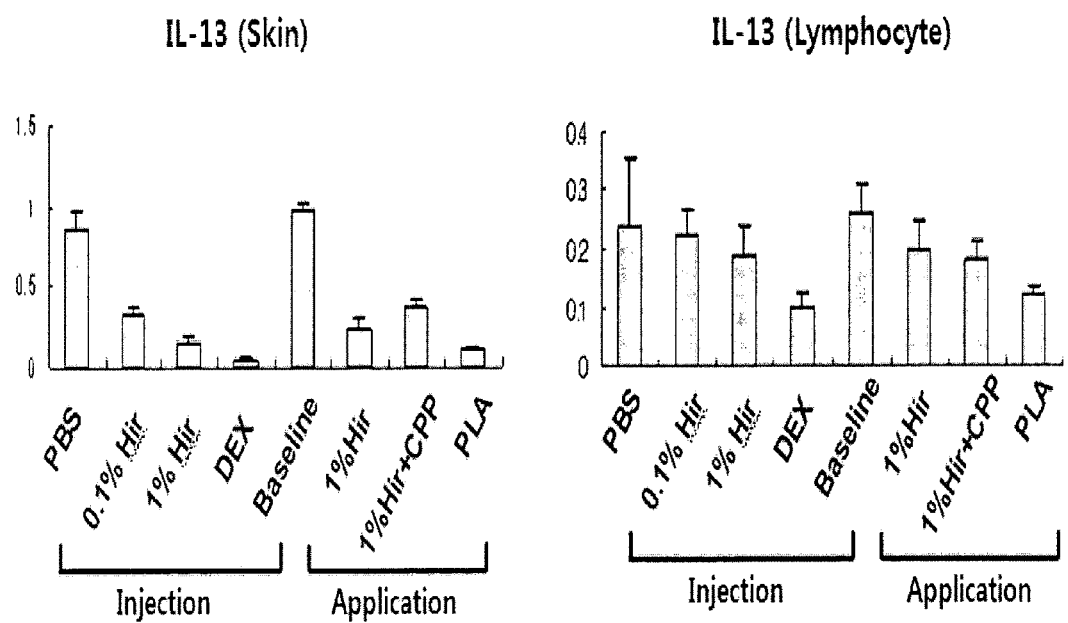
FIG. 9f is a graph showing IL-13 level measured by ELISA in the skin and lymph node from each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.

In addition, similar results in BABL/c mice in which atopic dermatitis had been induced were obtained (FIG. 9d, FIG. 9e and FIG. 9f).

IL-4 promotes cell proliferation of activated B cells and T cells and cell differentiation of naïve T cell (CD4$^+$T cell) towards Th2 cell. IL-4 expression level was increased in patients with atopic dermatitis. It could be appreciated that hirsutenone of the present invention plays inhibitory role in allergy response by reduction of IL-4 expression.

It has been known that IL-5 accelerates secretion of immunoglobulin by stimulating growth of B cells and acts as a major mediator of eosinophil activation. It was demonstrated that hirsutenone of the present invention significantly decreases the number of eosinophil in the subjects with atopic dermatitis by reducing IL-5 expression.

IL-13 is secreted in various cell types, particularly T helper cell type 2 (Th2) and plays as a critical mediator in allergic inflammation diseases. It was demonstrated that hirsutenone of this invention reduces IL-13 expression level, representing treatment efficacy of allergic inflammation diseases.

5. Measurement of COX-2 and iNOS Expression Using Real-time PCR

NC/Nga mice in which atopic dermatitis had been induced were treated with hirsutenone through an injection or skin application for 4 weeks and then mice epidermal cells were collected. To investigate whether hirsutenone has a regulatory activity on immune responses, the expression levels of COX-2 and iNOS were detected using real-time PCR. COX (cyclooxygenase) is an enzyme associated with formation of biological mediators called prostanoids. It is known that COX-1 is related to maintenance of homeostasis of human body, while COX-2 is associated with immune responses. In addition, iNOS (inducible Nitric Oxide Synthase) is an enzyme to produce NO (nitrix oxide) which regulates macrophages to play an important role in the initial immune responses against a microorganism invasion.

Figure 10B:
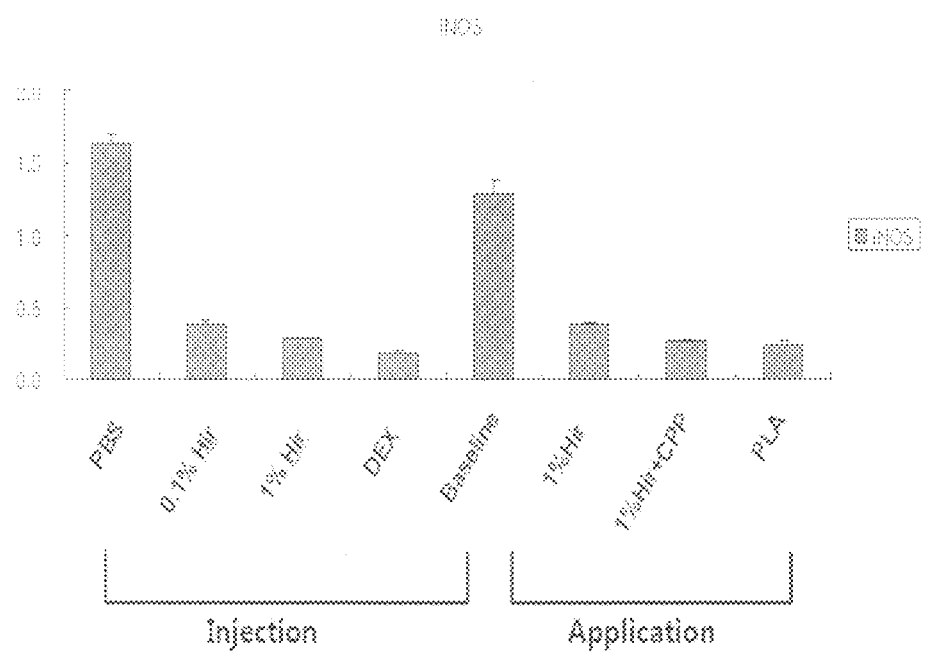
FIG. 10b is a graph showing a iNOS mRNA level detected by real-time PCR in each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.
Figure 10C:
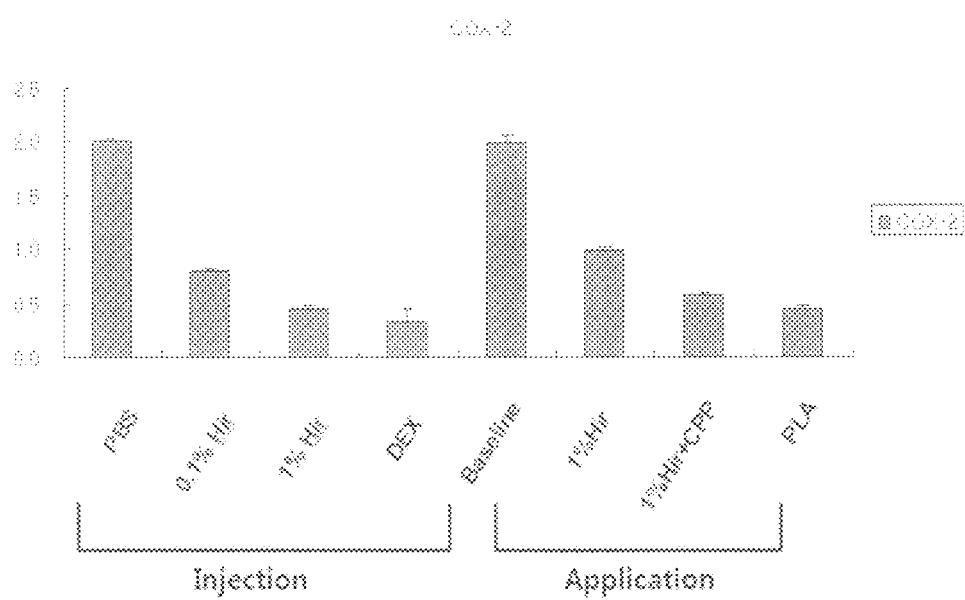
FIG. 10c is a graph showing a COX-2 mRNA level detected by real-time PCR in each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.
Figure 10D:
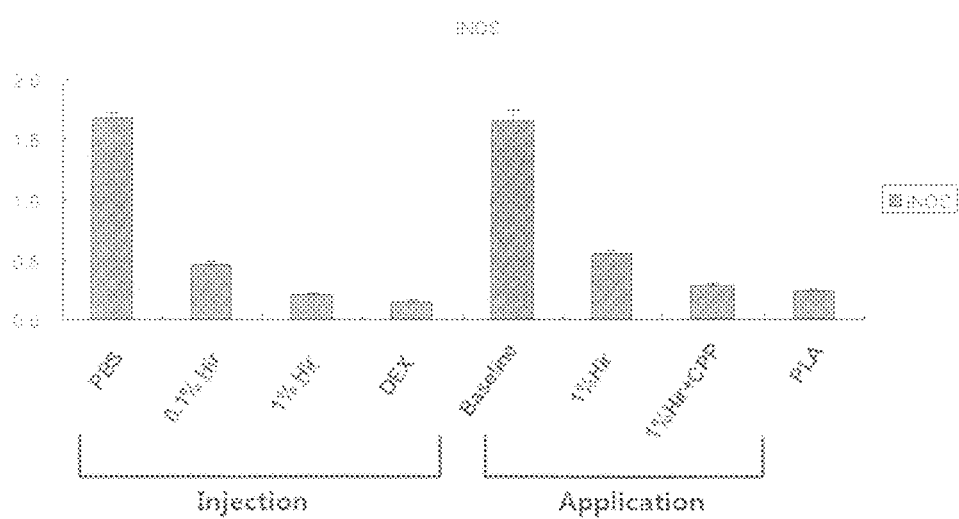
FIG. 10d is a graph showing a iNOS mRNA level detected by real-time PCR in each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.

As results, it was demonstrated that the expression levels of COX-2 and iNOS were significantly decreased in mice treated with hirsutenone through injection or skin application (FIGS. 10a-10b). In addition, similar results were obtained in the experiments with BABL/c mice in which atopic dermatitis had been induced (FIGS. 10c-10d).

6. Measurement of Cox-2 and iNOS Expression Level Using Western Blotting

Figure 11B:
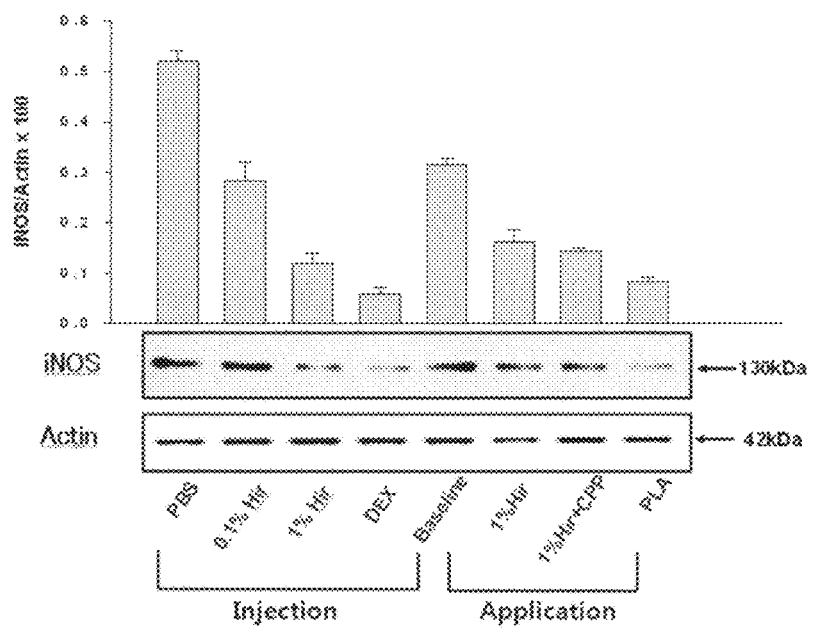
FIG. 11b is a graph showing a iNOS protein level measured by ELISA in each atopic dermatitis induced NC/Nga mouse before or after being administrated with PBS and a composition without an active ingredient as negative controls, dexamethasone (DEX) and plancol (PLA) as positive controls, and 0.1% and 1% hirsutenone (Hir) as an experimental group.

NC/Nga mice in which atopic dermatitis had been induced were treated with hirsutenone through an injection or skin application for 4 weeks and mice epidermal cells were collected. To investigate whether hirsutenone has a regulatory activity on immune responses, the expression levels of COX-2 and iNOS were detected using western blotting. It was demonstrated that the expression levels of COX-2 and iNOS were reduced in mice treated with hirsutenone (FIGS. 11a-11b) as same the results obtained by using real-time PCR.

Figure 11C:
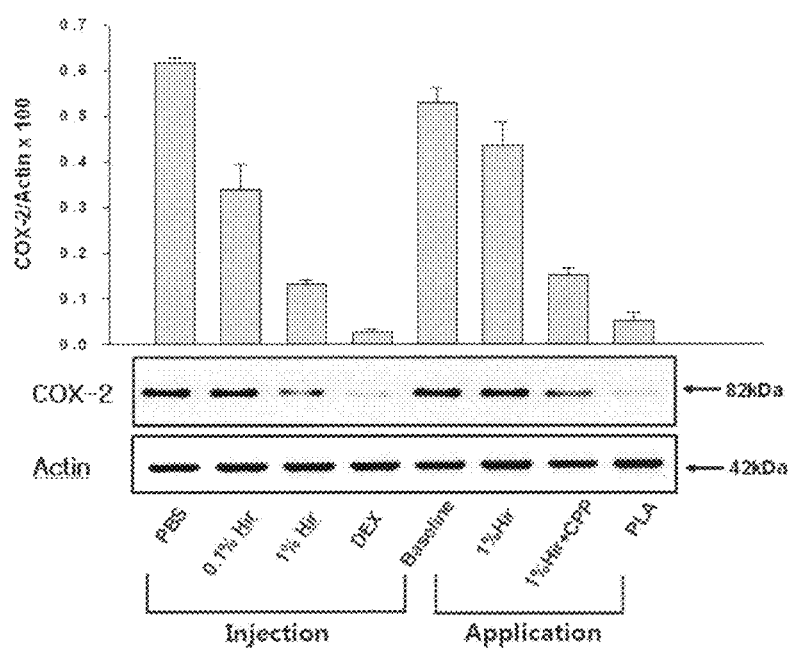
FIG. 11c is a graph showing a COX-2 level measured by ELISA in each atopic dermatitis induced BALB/c mouse before or after being administrated with PBS and a composition without an active ingredient as negative controls, dexamethasone (DEX) and plancol (PLA) as positive controls, and 0.1% and 1% hirsutenone (Hir) as an experimental group.

In addition, similar results in BABL/c mice in which atopic dermatitis had been induced were obtained (FIGS. 11c-11d).

As described above, it could be appreciated that hirsutenone of the present invention treats atopic dermatitis or relive a symptom of atopic dermatitis by regulation of immune response associated with atopic dermatitis.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating atopic dermatitis in a subject suffering from atopic dermatitis, which comprises contacting said subject with a composition comprising a therapeutically effective amount of an isolated compound represented by the following formula 1 or administering said composition to said subject; wherein the compound of formula 1 induces a reduction of eosinophil number, IgE level, or expression level of immune regulatory cytokine IL-4, IL-5 or IL-13

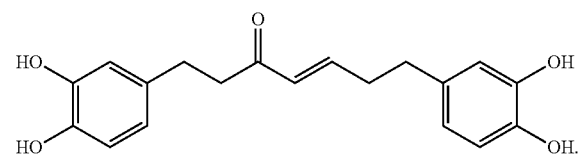

(1)

2. A method for relieving a symptom of atopic dermatitis in a subject suffering from atopic dermatitis, which comprises contacting said subject with a composition comprising an isolated compound represented by the following formula 1 or administering said composition to said subject; wherein the compound of formula 1 induces a reduction of eosinophil number, IgE level, or expression level of immune regulatory cytokine IL-4, IL-5 or IL-13

(1)

3. The method according to claim 2, wherein the composition is a cosmetic composition comprising a cosmetically effective amount of an isolated compound represented by the formula 1.

4. The method according to claim 2, wherein the composition is a functional food composition.

* * * * *

UNITED STATES PATENT AND TRADEMARK OFFICE
CERTIFICATE OF CORRECTION

PATENT NO. : 8,012,486 B2  Page 1 of 1
APPLICATION NO. : 12/454520
DATED : September 6, 2011
INVENTOR(S) : Lee et al.

It is certified that error appears in the above-identified patent and that said Letters Patent is hereby corrected as shown below:

In the Specification

Column 3, Formula 2, Lines 34-44, replace

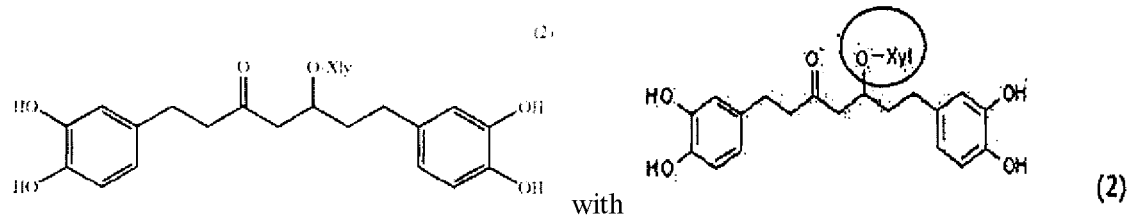

with

Signed and Sealed this
Eighteenth Day of March, 2014

Michelle K. Lee
*Deputy Director of the United States Patent and Trademark Office*